US007968569B2

(12) United States Patent
Zeldis

(10) Patent No.: US 7,968,569 B2
(45) Date of Patent: Jun. 28, 2011

(54) METHODS FOR TREATMENT OF MULTIPLE MYELOMA USING 3-(4-AMINO-1-OXO-1,3-DIHYDRO-ISOINDOL-2-YL)-PIPERIDINE-2,6-DIONE

(75) Inventor: Jerome B. Zeldis, Princeton, NJ (US)

(73) Assignee: Celgene Corporation, Summit, NJ (US)

( * ) Notice: Subject to any disclaimer, the term of this patent is extended or adjusted under 35 U.S.C. 154(b) by 145 days.

(21) Appl. No.: 10/438,213

(22) Filed: May 15, 2003

(65) Prior Publication Data

US 2004/0029832 A1 Feb. 12, 2004

Related U.S. Application Data

(60) Provisional application No. 60/380,842, filed on May 17, 2002, provisional application No. 60/424,600, filed on Nov. 6, 2002.

(51) Int. Cl.
*A61K 31/445* (2006.01)
(52) U.S. Cl. .................................................... 514/323
(58) Field of Classification Search .................. 514/321, 514/323
See application file for complete search history.

(56) References Cited

U.S. PATENT DOCUMENTS

| 3,536,809 | A |   | 10/1970 | Applezweig |   |
|---|---|---|---|---|---|
| 3,598,123 | A |   | 8/1971 | Zaffaroni et al. |   |
| 3,845,770 | A |   | 11/1974 | Theeuwes et al. |   |
| 3,916,899 | A |   | 11/1975 | Theeuwes et al. |   |
| 4,008,719 | A |   | 2/1977 | Theeuwes et al. |   |
| 4,810,643 | A |   | 3/1989 | Souza |   |
| 4,999,291 | A |   | 3/1991 | Souza |   |
| 5,059,595 | A |   | 10/1991 | Le Grazie |   |
| 5,073,543 | A |   | 12/1991 | Marshall et al. |   |
| 5,120,548 | A |   | 6/1992 | McClelland et al. |   |
| 5,134,127 | A |   | 7/1992 | Stella et al. |   |
| 5,229,496 | A |   | 7/1993 | Deeley et al. |   |
| 5,354,556 | A |   | 10/1994 | Sparks et al. |   |
| 5,385,901 | A |   | 1/1995 | Kaplan et al. |   |
| 5,391,485 | A |   | 2/1995 | Deeley et al. |   |
| 5,393,870 | A |   | 2/1995 | Deeley et al. |   |
| 5,528,823 | A |   | 6/1996 | Rudy, Jr. et al. |   |
| 5,580,755 | A |   | 12/1996 | Souza |   |
| 5,591,767 | A |   | 1/1997 | Mohr et al. |   |
| 5,593,990 | A |   | 1/1997 | D'Amato |   |
| 5,629,327 | A |   | 5/1997 | D'Amato |   |
| 5,635,517 | A | * | 6/1997 | Muller et al. | 514/323 |
| 5,639,476 | A |   | 6/1997 | Oshlack et al. |   |
| 5,674,533 | A |   | 10/1997 | Santus et al. |   |
| 5,698,579 | A |   | 12/1997 | Muller |   |
| 5,712,291 | A |   | 1/1998 | D'Amato |   |
| 5,731,325 | A |   | 3/1998 | Andrulis, Jr. et al. |   |
| 5,733,566 | A |   | 3/1998 | Lewis |   |
| 5,798,368 | A |   | 8/1998 | Muller et al. |   |
| 5,874,448 | A |   | 2/1999 | Muller et al. |   |
| 5,877,200 | A |   | 3/1999 | Muller |   |
| 5,929,117 | A |   | 7/1999 | Muller et al. |   |
| 5,955,476 | A |   | 9/1999 | Muller et al. |   |
| 6,020,358 | A |   | 2/2000 | Muller et al. |   |
| 6,071,948 | A |   | 6/2000 | D'Amato |   |
| 6,077,822 | A | * | 6/2000 | Dyrsting et al. | 514/8 |
| 6,114,355 | A |   | 9/2000 | D'Amato |   |
| 6,140,346 | A |   | 10/2000 | Andrulis, Jr. et al. |   |
| 6,228,879 | B1 |   | 5/2001 | Green et al. |   |
| 6,235,756 | B1 |   | 5/2001 | D'Amato |   |
| 6,281,230 | B1 | * | 8/2001 | Muller et al. | 514/323 |
| 6,316,471 | B1 |   | 11/2001 | Muller et al. |   |
| 6,326,388 | B1 |   | 12/2001 | Man et al. |   |
| 6,335,349 | B1 |   | 1/2002 | Muller et al. |   |
| 6,380,239 | B1 |   | 4/2002 | Muller et al. |   |
| 6,395,754 | B1 |   | 5/2002 | Muller et al. |   |
| 6,403,613 | B1 |   | 6/2002 | Man et al. |   |
| 6,420,414 | B1 |   | 7/2002 | D'Amato |   |
| 6,458,810 | B1 |   | 10/2002 | Muller et al. |   |
| 6,469,045 | B1 |   | 10/2002 | D'Amato |   |
| 6,476,052 | B1 |   | 11/2002 | Muller et al. |   |
| 6,518,298 | B2 |   | 2/2003 | Green et al. |   |
| 6,555,554 | B2 | * | 4/2003 | Muller et al. | 514/323 |
| 6,673,828 | B1 |   | 1/2004 | Green et al. |   |
| 7,119,106 | B2 | * | 10/2006 | Muller et al. | 514/323 |
| 7,189,740 | B2 | * | 3/2007 | Zeldis | 514/323 |
| 7,393,862 | B2 | * | 7/2008 | Zeldis | 514/320 |
| 7,435,745 | B2 |   | 10/2008 | D'Amato |   |

(Continued)

FOREIGN PATENT DOCUMENTS

WO   WO 92/14455   9/1992

(Continued)

OTHER PUBLICATIONS

Corral et al. Immunomodulation by thalidomide and thalidomide analogues . . . Ann. Rheum. 1999; 58; 107-13.*
Kyle et al. ("The Application of Thalidomide in Multiple Myeloma", Semin Oncol. Dec. 2001; 28(6):583-7).*
Davies et al. ("Thalidomide and immunomodulatory derivatives augment natural killer cell cytotoxicity in multiple myeloma", Blood. Jul. 1, 2001;98(1):210-6).*
Broder et al. ("Dideoxycytidine: current clinical experience and future prospects. A summary.", Am J Med. May 21, 1990;88(5B):31S-33S).*
Filella et al. (Cancer Detect Prey. 1996;20(1):52-6).*
Raza et al., 2001, "Thalidomide produces transfusion independence in long-standing refractory anemias of patients with myelodysplatic syndromes," Blood 98(4):958-965.

(Continued)

*Primary Examiner* — Frederick Krass
*Assistant Examiner* — Chris E Simmons
(74) *Attorney, Agent, or Firm* — Jones Day

(57) ABSTRACT

Methods of treating, preventing and/or managing cancer as well as and diseases and disorders associated with, or characterized by, undesired angiogenesis are disclosed. Specific methods encompass the administration of an immunomodulatory compound alone or in combination with a second active ingredient. The invention further relates to methods of reducing or avoiding adverse side effects associated with chemotherapy, radiation therapy, hormonal therapy, biological therapy or immunotherapy which comprise the administration of an immunomodulatory compound. Pharmaceutical compositions, single unit dosage forms, and kits suitable for use in methods of the invention are also disclosed.

15 Claims, 1 Drawing Sheet

U.S. PATENT DOCUMENTS

Figure 1:
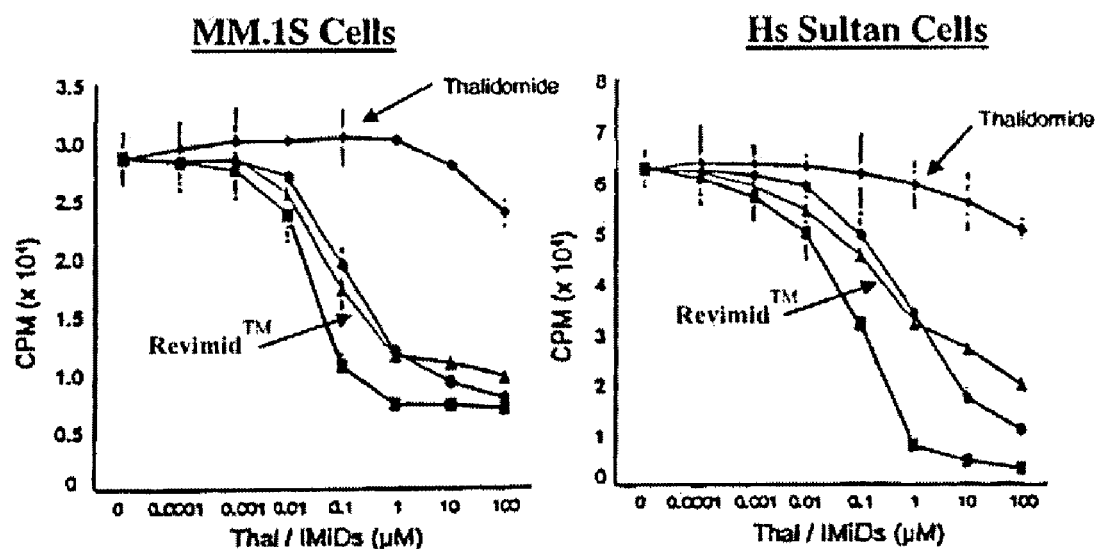

| | | | |
|---|---|---|---|
| 2001/0018445 A1 | 8/2001 | Huang et al. | |
| 2001/0022973 A1* | 9/2001 | Ortyl et al. | 424/452 |
| 2001/0056114 A1 | 12/2001 | D'Amato | |
| 2002/0035090 A1 | 3/2002 | Zeldis et al. | |
| 2002/0045643 A1 | 4/2002 | Muller et al. | |
| 2002/0052398 A1 | 5/2002 | D'Amato | |
| 2002/0054899 A1 | 5/2002 | Zeldis | |
| 2002/0061923 A1 | 5/2002 | D'Amato | |
| 2002/0128228 A1 | 9/2002 | Hwu | |
| 2002/0161023 A1 | 10/2002 | D'Amato | |
| 2002/0173658 A1 | 11/2002 | Muller et al. | |
| 2002/0183360 A1 | 12/2002 | Muller et al. | |
| 2003/0013739 A1 | 1/2003 | Masferrer et al. | |
| 2003/0028028 A1 | 2/2003 | Man et al. | |
| 2003/0045552 A1 | 3/2003 | Robarge et al. | |
| 2003/0069428 A1 | 4/2003 | Muller et al. | |
| 2003/0096841 A1 | 5/2003 | Robarge et al. | |
| 2003/0139451 A1 | 7/2003 | Shah et al. | |
| 2003/0144325 A1 | 7/2003 | Muller et al. | |
| 2003/0181428 A1 | 9/2003 | Green et al. | |
| 2003/0187024 A1 | 10/2003 | D'Amato | |
| 2003/0191098 A1 | 10/2003 | D'Amato | |
| 2003/0235909 A1 | 12/2003 | Hariri et al. | |
| 2004/0029832 A1 | 2/2004 | Zeldis | |
| 2004/0067953 A1* | 4/2004 | Stein et al. | 514/251 |
| 2004/0077685 A1 | 4/2004 | Figg et al. | |
| 2004/0077686 A1 | 4/2004 | Dannenberg et al. | |
| 2004/0087546 A1 | 5/2004 | Zeldis | |
| 2004/0091455 A1 | 5/2004 | Zeldis | |
| 2004/0122052 A1 | 6/2004 | Muller et al. | |
| 2004/0147558 A1* | 7/2004 | Treston et al. | 514/323 |
| 2004/0266809 A1 | 12/2004 | Emanuel et al. | |
| 2005/0049265 A1* | 3/2005 | Adams | 514/267 |

FOREIGN PATENT DOCUMENTS

| | | |
|---|---|---|
| WO | WO 94/20085 | 9/1994 |
| WO | WO 98/03502 | 1/1998 |
| WO | WO 98/54170 | 12/1998 |
| WO | WO 01/70275 | 9/2001 |
| WO | WO 01/87307 | 11/2001 |
| WO | WO 02/015926 | 2/2002 |
| WO | WO 02/059106 | 8/2002 |
| WO | WO 02/064083 | 8/2002 |
| WO | WO03086373 | 10/2003 |

OTHER PUBLICATIONS

Shah et al., 1999, "Synthesis and enantiomeric separation of 2-phthalimidino-glutaric acid analogues: potent inhibitors of tumor metastasis," J. Med. Chem. 42:3014-3017.

Shibata et al., 1995, "N-alkylphthalimides: structural requirement of thalidomidal action on 12-0-tetradecanoylphorbol-13-acetate-induced tumor necrosis factor a production by human leukemia HL-60 cells," Chem. Pharm. Bull. 43(1):177-179.

Shimazawa et al., 1999, "Antiangiogenic activity of tumor necrosis factor-alpha production regulators derived from thalidomide," Biol. Pharm. Bull. 22(2):224-226.

Rubin et al, "Principles of Cancer Treatment-l", 12 ONCO IV I, May 2003.

Wilen et al., 1977, Tetrahedron 33:2725.

Wilen, 1972, *Tables of Resolving Agents and Optical Resolutions*, E.L. Eliel, ed., Univ. of Notre Dame Press, Notre Dame, IN pp. 268.

Wolff ed., 1995, *Burger's Medicinal Chemistry and Drug Discovery*, 5th ed.., pp. 172-178, 949-982.

Bach, 1963, "Thalidomide in Cancer Chemotherapy," *The Lancet*, No. 1271, p. 71.

Bach, 1963, "Studies on the Possible Anti-Neoplastic Effect of Thalidomide," *Acta Pathologica Et Microbiologica Scandinavica* 59:491-499.

Chaundhry, 1966, *Cancer Research*, "Effect of Prednisolone and Thalidomide on Induced Submandibular Gland Tumors in Hamster," 26(part 1)1884-86.

DiPaolo, 1963, "Effect of Thalidomide on a Variety of Transplantable Tumors," *Cancer Chemotherapy Reports* No. 29, p. 99-102.

DiPaolo, 1963, "In vitro Test Systems for Cancer Chemotherapy, II. Correlation of in vitro Inhibition of Dehydrogenase and Growth with in vivo Inhibition of Ehrlich Asoites Tumor," *Proceedings of the Society for Experimental Biology & Medicine*, 114:384-387.

DiPaolo, 1964, "Thalidomide: Effects on Ehrlich Ascites Tumor Cells in vitro" Science 144:1583.

Mauad, 1963, "Clinical Improvements Obtained in Advanced Caner Patients with Treatment with Thalidomide Associated with Hormones," Anais *Paulistas de Medicina e Cirurgia* 86:13-40.

Roe and Mitchley, 1963, "Thalidomide and Neoplasia" *Nature* 200:1016-1017.

Alexanian et al., 2004, "VTD (Velcade, thalidomide, dexamethasone) as primary therapy for newly-diagnosed multiple myeloma," Am. Soc. Hematol. 46th Ann. Meeting Dec. 4-7, 2004, San Diego, CA Abstract #210.

Anderson, 2000, "Thalidomide: Therapeutic potential in hematologic malignancies," Seminars in Hematology 37(1 Supp 3): 1-4.

Attal et al., 2004, "Maintenance treatment with thalidomide after autologous transplantation for myeloma: First analysis of a prospective randomized study of the Intergroupe Francophone du Myelome (IFM 99 02)," Am. Soc. Hematol. 46th Ann. Meeting Dec. 4-7, 2004, San Diego, CA Abstract #535.

Bemardeschi et al., 2003, J. Exp. Clin. Cancer Res. 22(4):129-133.

Corral et al., 1999, "Differential cytokine modulation and T cell activation by two distinct classes of thalidomide analogues that are potent inhibitors of TNF-alpha," J. Immunol. 163(1):380-386.

Davies et al., 2001, "Thalidomide and immunomodulatory derivatives augment natural killer cell cytotoxicity in multiple myeloma," Blood 98(1):210-216.

Dimopoulos et al., 2004, "Primary treatment with puilsed melphalan, dexamethasone, thalidomide (MDT) for symptomatic patients with multiple myeloma $\geq$75 years of age," Am. Soc. Hematol. 46th Ann. Meeting Dec. 4-7, 2004, San Diego, CA Abstract #1482.

Eisen et al., 2000, "Continuous low dose Thalidomide: a phase II study in advanced melanoma, renal cell, ovarian and breast cancer," Br. J. Cancer 82(4):812-817.

Fakhouri et al., 2004, "Thalidomide in patients with multiple myeloma and renal failure," Br. J. Haematol. 125:90-102.

Fenk et al., 2005, "Single-agent thalidomide for treatment of first relapse following high-dose chemotherapy in patients with multiple myeloma," Leukemia 19(1):156-159.

Gupta et al., 2001, "Adherence of multiple myeloma cells to bone marrow stromal cells upregulates vascular endothelial growth factor secretion: therapeutic applications," Leukemia 15(12):1950-1961.

Haslett et al., 2003, "Thalidomide and a thalidomide analogue drug costimulate virus-specific CD8+ T cells in vitro," J. Infect. Dis. 187(6):946-955.

Hideshima et al., 2000, "Thalidomide and its analogs overcome drug resistance of human multiple myeloma cells to conventional therapy," Blood 96(9):2943-2950.

Offidani et al., 2003, Thalidomide plus oral melphalan for advanced multiple myeloma: a phase II study. Haematologica. Dec. 2003;88(12):1432-1433.

Palumbo et al., 2004, "A prospective randomized trial of oral melphalan prednisone, thalidomide (MPT) vs. oral melphalan, prednisone (MP): An interim analysis," Am. Soc. Hematol. 46th Ann. Meeting Dec. 4-7, 2004, San Diego, CA Abstract #207.

Raje et al., 1999, "Thalidomide—a revival story," N. Engl. J. Med. 341(21):1606-1609.

Rajkumar et al., 2004, "Thalidomide plus dexamethasone versus dexamethasone alone in newly diagnosed multiple myeloma (E1A00): Results of a phase III trial coordinated by the Eastern Cooperative Oncology Group," Am. Soc. Hematol. 46th Ann. Meeting Dec. 4-7, 2004, San Diego, CA Abstract #205.

Rajkumar et al., 2000, "Prognostic value of bone marrow angiogenesis in multiple myeloma," Clin. Cancer Res. 6(8):3111-3116.

Ribatti et al., 1999, "Bone marrow angiogenesis and mast cell density increase simultaneously with progression of human multiple myeloma," Br. J. Cancer 79(3-4):451-455.

Singhal et al., 1999, Antitumor activity of thalidomide in refractory multiple myeloma, N. Engl. J. Med. 341(21):1565-1571.

Steins et al., 2002, "Efficacy and safety of thalidomide in patients with acute myeloid leukemia," Blood 99(3):834-839.

Vacca et al., 1999, "Bone marrow neovascularization, plasma cell angiogenic potential, and matrix metalloproteinase-2 secretion parallel progression of human multiple myeloma," Blood 93(9):3064-3073.

Wohrer et al., 2004, "Effective treatment of primary plasma cell leukemia with thalidomide and dexamethasone—a case report," Hematol. J. 5(4):361-363.

N. Ake Jonnson, 1972, "Chemical Structure and Teratogenic Properties," Acta Pharm., pp. 521-542.

Anderson, "Moving disease biology from the laboratory to the clinic," *Seminars in Oncology*, 2002 29:17-20.

Barlogie et al., "Total Therapy II (TTII) for newly diagnosed multiple myeloma (MM): preliminary data on feasibility and efficacy in the first 231 enrolled patients; comparison with predecessor trial total therapy I ((TTI) (N=231)," *Blood, Abstract # 2857*, Dec. 7-11, 2001, *American Society of Hematology*.

Barlogie et al., "High-dose therapy immunomodulatory drugs in multiple myeloma," *Seminars in Oncology*, 2002, 29 (6):26-33.

Barlogie et al., "Introduction: Thalidomide and the IMiDs in multiple myeloma," *Seminars in Hematology*, 2003, 40 (4):1-2.

Barlogie, "Thalidomide and CC-5013 in Multiple Myeloma: The University of Arkansas experience," *Seminars in Hematology*, 2003, 40 (4):33-38.

Bartlett et al., "The evolution of thalidomide and its IMiD derivatives as anticancer agents," *Nature Reviews Cancer*, 2004, 4 (4):1-9.

Bartlett et al., "Phase I study to determine the safety, tolerability and immunostimulatory activity of thalidomide analogue CC-5013 in patients with metastatic malignant melanoma and other advanced cancers," *British Journal of Cancer*, 2004, 90:955-961.

Battegay, "Angiogenesis: mechanistic insights, neovascular diseases, and therapeutic prospects," *J. Mol. Med.*, 1995, 73:333-346.

Baz et al., "Doxil (D), vincristine (V), reduced frequency dexamethasone (d) and revlimid (R) (DVd-R) results in a high response rate in patients with refractory multiple myeloma (RMM)," *Blood, Abstract # 2559, American Society of Hematology*, Dec. 10-13, 2005.

Brennen et al., "Thalidomide and analogues: current proposed mechanisms and therapeutic usage," *Clinical Prostate Cancer*, 2004, 3 (1):54-61.

Celgene Corporation, "Celgene advances immunomodulatory drug (IMiD™) clinical program," Press Release, Feb. 2000.

Celgene Corporation, "Initial Phase I solid tumor data on Celgene's lead ImiD™, Revimid™," Press Release, Jun. 2001.

Celgene Corporation, "Celgene Corporation receives orphan drug designation for Revimidn™ for multiple myeloma," Press Release, Oct. 2001.

Celgene Corporation, "Celgene Corporation announces third quarter results. Thalomid® (thalidomide) sales increase 24%. Prescriptions up 50%. Enhanced S.T.E.P.S.® launched. Pilot d-MPH data presented," Press Release, Oct. 2001.

Celgene Corporation, "Celgene expands clinical development program for Revimid™ —Five additional trials of Revimid initiated in hematological and solid tumor cancers," Press Release, Jun. 2002.

Celgene Corporation, "Celgene Corporation announces third quarter results. THALOMID® (thalidomide) revenue increases 41% to $30.5 million. Pivotal programs for THALOMID and REVIMID™ finalized. Peer-reviewed publications of THALOMID and REVIMID data. First JNK inhibitor advanced to Phase I clinical trial," Press Release, Oct. 2002.

Celgene Corporation, "Blood reports Revimid™ has anti-tumor activity in patients with relapsed and refractory multiple myeloma," Press Release, Nov. 1, 2002.

Celgene Corporation, "Celgene provides update on clinical pipeline. Celgene Announces first target indication for ACTIMID™, CC-8490. SeICID™ program to advance based on results from Phase I/II trial of CC-1088. First JNK inhibitor successfully completes phase I trial," Press Release, Jan. 2003.

Celgene Corporation, "Celgene Corporation announces fourth quarter and full year results for 2002," Press Release, Jan. 2003.

Celgene Corporation, "Celgene receives fast track status from FDA for Revimid™ in multiple myloma," Press Release, Feb. 2003.

Celgene Corporation, "Celgene receives fast track status from FDA for Revimid™ in myelodysplastic sydromes," Press Release, Apr. 2003.

Celgene Corporation, "New Revimid™ clinical data shows potential as novel approach to treating myelodysplastic syndromes (MDS)," Press Release, May 2003.

Celgene Corporation, "Celgene corporation reports strong operating performance in second quarter as total sales increase 100 percent and profits rise," Press Release, Jul. 2003.

Celgene Corporation, "Celgene corporation reports record operating performance in third quarter as total revenue increases 117% and profits rise," Press Release, Oct. 2003.

Celgene Corporation, "Celgene corporation advances ACTIMID™ (CC-4047) into phase II trial for prostate cancer," Press Release, Oct. 2003.

Celgene Corporation, "Additional clinical data presented on Revimid™ in myelodysplastic sydromes at the American Society of Hematology $45^{th}$ annual meeting," Press Release, Dec. 2003.

Celgene Corporation, "Celgene corporation reviews 2003 achievements and announces 2004 financial outlook," Press Release, Jan. 2004.

Celgene Corporation, "Revlimid™ receives orphan drug designation from the European commission for multiple myeloma," Press Release, Feb. 2004.

Celgene Corporation, "Revlimid™ receives orphan drug designation from the European commission for myelodysplastic sydromes," Press Release, Mar. 2004.

Celgene Corporation, "Celgene corporation reports record operating performance in first quarter with strong revenue growth and profits," Press Release, Apr. 2004.

Celgene Corporation, "Celgene announces plans to stop phase III trials in melanoma due to lack of efficacy," Press Release, Apr. 2004.

Dalgleish, et al., "New thalidomide analogues; anti-cancer, anti-angiogenic and immunostimulatory," *British Journal of Cancer*, 2001, 85 (1)25.

Dalgleish et al., "Thalidomide analogues CC-5013 and CC-4047 induce T cell activation and IL-12 production in patients with both solid tumours and relapsed and refractory multiple myeloma," *British Journal of Cancer*, 2003, 88(Suppl I), S25-S54.

Database Pharmaml XP002369094 retrieved from STN. Database accession No. 1659300, & Marketletter, Oct. 9, 2001.

Database NLDB XP002369095 retrieved from STN. Database accession No. 2002:35280, & Marketletter, Jun. 18, 2001.

Davies et al., "Thalidomide (Thal) and immunomodulatory derivatives (IMiDs) augment natural killer (NK) cell cytotoxicity in multiple myeloma(MM))," Abstract # 3617, *American Society of Hematology*, Dec. 1-5, 2000.

Davies et al., "Thalidomide (Thal) and immunomodulatory derivatives (IMiDs) augment natural killer (NK) cell cytotoxicity in multiple myeloma ~MM)," Abstract # P222, *VIIIth International Myeloma Workshop*, May 4-8, 2001.

Dibbs et al., "Thalidomide and thalidomide analogs suppress TNFα secretion by myocytes," Abstract # 1284, *Circulation*, 1998.

Dimopoulos et al., "Results of thalidomide and IMIDs in multiple myeloma,", Abstract # P12.1.4, *International Multiple Myeloma Workshop*, May 23-27, 2003.

Dimopoulos et al., "Treatment of plasma cell dyscrasias with thalidomide and its derivatives," *Journal of Clinical Oncology*, Dec. 1, 2003, 21 (23)4444-4454.

Dimopoulos et al., "Study of lenalidomide plus dexamethasone versus dexamethasone alone in relapsed or refractory multiple myeloma (MM): Results of a phase 3 Study (MM-010)," Abstract # 6, *American Society of Hematology*, Dec. 10-13, 2005.

Dredge et al., A costimulatory thalidomide analog enhances the partial anti-tumor immunity of an autologous vaccination in a model of colorectal cancer, Abstract # 491, *American Association for Cancer Research*, Apr. 6-10, 2002.

Dredge et al., "Adjuvants and the promotion of Th1-type cytokines in tumour immunotherapy," *Cancer Immunol. Immunother.*, 2002, 51:521-531.

Dredge et al., "Immunological effects of thalidomide and its chemical and functional analogs," *Critical Reviews in Immunology*, 2002, 21 (5&6):425-437.

Dredge et al., "Protective antitumor immunity induced by a costimulatory thalidomide analog in conjunction with whole tumor cell vaccination is mediated by increased Th1 -type immunity[1]," *The Journal of Immunology*, 2002, 168:4914-4919.

Dredge et al., "Recent developments in antiangiogenic therapy," *Expert Opin. Biol. Ther.*, 2002, 2 (8):953-966.

Dredge et al., "Angiogenesis inhibitors in cancer therapy," *Current Opinion in Investigational Drugs*, 2003, 4 (6):667-674.

Dredge et al., "Thalidomide analogs as emerging anti-cancer drugs," *Anti-Cancer Drugs*, 2003, 14:331-335.

Fickentscher et al., "Stereochemical properties and teratogenic activity of some tetrahydrophthalimides," *Molecular Pharmacology*, 1976, 13:133-141.

Figg et al., "Inhibition of angiogenesis: treatment options for patients with metastatic prostate cancer," *Investigational New Drugs*, 2002, 20(2):183-194.

Galustian et al., "Thalidomide-derived immunomodulatory drugs as therapeutic agents," *Expert Opin. Biol. Ther.*, 2004, 4 (12):1-8.

Glaspy et al., "The potential role of thalidomide and thalidomide analogs in melanoma," *Clinical Advances in Hematology & Oncology*, 2004, 1-7.

Gupta et al., "Adherence of multiple myeloma cells to bone marrow stromal cells upregulates vascular endothelial growth factor secretion: therapeutic applications," *Leukemia*, 2001, 15:1950-1961.

Hayashi et al., "Mechanisms whereby immunomodulatory analogs of thalidomide augment autologous NK cell anti-myeloma immunity," *Blood Abstract #3219*, Dec. 6-10, 2002, *American Society of Hematology*.

He, W., et al., 1993, Abstract of papers, 206th American Chemical Society, Chicago, IL; Med. Chem., paper 216.

Helm et al., "Comparative teratological investigation of compounds of structurally and pharmacologically related to thalidomide," *Arzneimittel Forschung/Drug Research*, 1981, 31 (I)941-949.

Hernandez-Illizaliturr et al., "Addition of immunomodulatory drugs CC5013 or CC4047 to rituximab enhances anti-tumor activity in a severe combined immunodeficiency (SCID) mouse lymphoma model," Abstract # 235, *American Society of Hematology*, Dec. 6-9, 2003.

Hideshima et al., "Thalidomide and its analogs overcome drug resistance of human multiple myeloma cells to conventional therapy," *Blood*, 2000, 96:2943-2950, *American Society of Hematology*.

Hideshima et al., "Thalidomide (Thal) and its analogs overcome drug resistance of human multiple myeloma (MM) cells to conventional therapy," Abstract 1313. *American Society of Hematology*, Dec. 1-5, 2000.

Hunt et al., "Markers of endothelial and haemostatic activation in the use of CC-4047, a structural analogue of thalidamide, in relapsed myeloma," *Blood Abstract # 3216*, Dec. 6-10, 2002, *American Society of Hematology*.

Hussein et al., "Doxil (D), vincristine (V), reduced frequency dexamethasone (d) and Revlimid (DVd-R) a phase I/II trial in advanced relapsed/refractory multiple myeloma (Rmm) patients," *Blood, Abstract #208, American Society of Hematology*, Dec. 4-7, 2004.

Hwu et al., "Thalidomide and its analogues in the treatment of metastatic melanoma," *Chemotherapy Foundation Symposium*, Abstract #44, 2002.

Kyle, "Current therapy of multiple myeloma," *Internal Medicine*, 2002, 41 (3)175-180.

Kyle et al., "Multiple myeloma," *New England Journal of Medicine*, 2004, 351:1860-1873.

LeBlanc et al., "Immunomodulatory drug costimulates T cells via the B7-CD28 pathway," *Blood*, 2004, 103:1787-1790, *American Society of Hematology*.

Lentzsch et al., "In vivo activity of thalidomide and immunomodulatory drugs against multiple myeloma," *VIIIth International Myeloma Workshop. Abstract #P225*, May 4-8, 2001.

Lentzsch et al., "Immunomodulatory derivative of thalidomide (IMiD CC-4047) determine the lineage commitment of hematopoietic progenitors by down regulation of GATA-1 and modulation of cytokine secretion," Abstract # 3073, *American Society of Hematology*, Dec. 6-9, 2003.

Lentzsch et al., "Immunomodulatory derivative of thalidomide (IMiD CC-4047) down regulates CAAT/enhancer-binding protein $^\beta$(C/EBP$^\beta$) in multiple myeloma (MM)," Abstract # 3456, *American Society of Hematology*, Dec. 6-9, 2003.

Luzzio et al., "Thalidomide analogues: derivatives of an orphan drug with diverse biological activity," *Expert Opin. Ther. Patents*, 2004, 14 (2):215-229.

Man et al., "α- Fluoro-substituted thalidomide analogues," *Bioorganic & Medicinal Chemistry Letters 13*, 2003, 3415-3417.

Marriott et al., "Immunotherapeutic and antitumour potential of thalidomide analogues," *Expert Opin. Biol. Ther.*, 2001, 1 (4):1-8.

Marriott et al., "New thalidomide analogues; anti-cancer, anti-angiogenic and immunostimulatory," *British Journal of Cancer*, 85:25, Jul. 6, 2001.

Marriott et al., "Thalidomide and its analogues have distinct and opposing effects on TNF-α and TNFR2 during co-stimulation of both CD4$^+$and CD8$^+$T cells," *Clin. Exp. Immunol.*, 2002, 130:75-84.

Marriott et al., "A novel subclass of thalidomide analogue with anti-solid tumor activity in which caspase-dependent apoptosis is associated with altered expression of bcl-2 family proteins[1]," *Cancer Research*, 2003, 63:593-599.

Marriott et al., "Thalidomide derived immunomodulatory drugs (IMiDs) as potential therapeutic agents," *Current Drug Targets— Immune. Endocrine & Metabolic Disorders*, 2003, 3:181-186.

Masellis et al., "Changes in gene expression in bone marrow mesenchymal progenitor cells as a consequence of IMiD therapy in multiple myeloma patients," *Blood, Abstract #1548*, Dec. 7-11, 2001, *American Society of Hematology*.

McCarty, "Thalidomide may impede cell migration in primates by down-regulating integrin β-chains: potential therapeutic utility in solid malignancies, proliferative retinopathy, inflammatory disorders, neointimal hyperplasia, and osteoporosis," *Medical Hypotheses*, 1997, 49:123-131.

Mitsiades et al., "Apoptic signaling induced by immunomodulatory thalidomide analogs (Imids) in human multiple myeloma cells: therapeutic implications," Abstract # 3224, Dec. 7-11, 2001, *American Society of Hematology*.

Mitsiades et al., "Apoptic signaling induced by immunomodulatory thalidomide analogs in human multiple myeloma cells: therapeutic implications," *Blood*, 2002, 99:4525-4530, *American Society of Hematology*.

Mitsiades et al., "CC-5013 Celgene," *Current Opinion in Investigational Drugs*, 2004, 5 (6):635-647.

Moutouh et al., "Novel immunomodulatory drugs (IMiD®): A potential, new therapy for β- hemoglobinopathies," Abstract # 3740, *American Society of Hematology*, Dec. 4-7, 2004.

Patten et al., "The early use of the serum free light chain assay in patients with relapsed refractory myeloma receiving treatment with a thalidomide analogue (CC-4047)," Abstract # 1640, *American Society of Hematology*, Dec. 6-9, 2003.

Payvandi et al., "Effects of a thalidomide analog on binding activity of transcription factors and cell cycle progression of multiple myeloma cell lines," *Blood Abstract #2487*, Dec. 1-5, 200, *American Society of Hematology*.

Payvandi et al., "The thalidomide analogs IMiDs enhance expression of CD69 stimulatory receptor on natural killer cells," Abstract # 1793, *American Association for Cancer Research*, Mar. 24-28, 2001.

Payvandi et al., "Thaliomide analogs IMiDs inhibit expression of cyclooxygenase-2 in multiple myeloma cell line and LPS stimulated PBMCs," *Blood, Abstract #2689*, Dec. 7-11, 2001, *American Society of Hematology*.

Payvandi et al., "Thalidomide and IMiDS inhibit microvessel formation from human arterial rings in the absence of human liver microsomes," *Blood, Abstract # 5046*, Dec. 6-10, 2002, *American Society of Hematology*.

Payvandi et al., "CC-5013 inhibits the expression of adhesion molecules ICAM-1 and CD44 and prevents metastasis of B16 F10 mouse melanoma cells in an animal model," *American Society of Clinical Oncology, Abstract # 992*, 2003.

Payvandi et al., "Immunomodulatory drugs inhibit expression of cyclooxygenase-2 from TNF-α, IL-1β, and LPS-stimulated stimulated human PMBC in a partially IL-10-dependent manner," *Cellular Immunology*, 2004, 81-88.

Raje et al., "Combination of the mTOR inhibitor rapamycin and CC-5013 has synergistic activity in multiple myeloma," *Blood*, Dec. 15, 2004, 104 (13)4188-4193.

Rajkumar et al., "Combination therapy with lenalidomide plus dexamethasone (Rev/Dex) for newly diagnosed myeloma," *Blood*, Dec. 15, 2005, 106 (13)4050-4053.

Richardson et al., "A Phase 1 study of oral CC5013, an immunomodulatory thalidomide (Thal) derivative, in patients with relapsed and refractory multiple myeloma (MM)," *Blood Abstract #3225*, Dec. 7-11, 2001, *American Society of Hematology*.

Richardson et al., "Immunomodulatory drug CC-5013 overcomes drug resistance and is well tolerated in patients with relapsed multiple myeloma," *Blood*, 2002 100:3063-3067, *American Society of Hematology*.

Richardson et al., "A multi-center, randomized, phase 2 study to evaluate the efficacy and safety of 2 CDC-5013 dose regimens when used alone or in combination with dexamethasone (Dex) for the treatment of relapsed or refractory multiple myeloma (MM)," *Blood, Abstract # 825, American Society of Hematology*, Dec. 6-9, 2003.

Richardson et al., "Immunomodulatory analogs of thalidomide: an emerging new therapy in myeloma," *Journal of Clinical Oncology*, 2004, 22(16) 3212-3214.

Richardson et al., "A multicenter, single-arm, open-label study to evaluate the efficacy and safety of single-agent lenalidomide in patients with relapsed and refractory multiple myeloma; preliminary results," *10$^{th}$ International Myeloma Workshop*, Apr. 10-14, 2005.

Richardson et al., "Novel biological therapies for the treatment of multiple myeloma," *Best Practice & Research Clinical Haematology*, 2005, 18 (4):619-634.

Richardson et al., "A phase 1 trial of lenalidomide (REVLIMID® ) with bortezomib (VELCADE® in relapsed and refractory multiple myeloma," *Blood, Abstract # 365, American Society of Hematology*, Dec. 10-13, 2005.

Rubin et al., "Principles of cancer treatment-1," 2003, 12 ONCO IV 1.

Schafer et al., "Enhancement of cytokine production and AP-1 transcriptional activity in T cells by thalidomide-related immunomodulatory drugs," *Journal of Pharmacology and Experimental Therapeutics*, 2003, 305(3)1222-1232.

Schey et al., "A phase I study of an immunomodulatory thalidomide analog, CC-4047, in relapsed or refractory multiple myeloma," *Journal of Clinical Oncology*, 2004, 22 (16):1-8.

Schey et al., "A phase I study of an immunomodulatory thalidomide analogue (CC4047) in relapse/refractory multiple myeloma," *International Society for Experimental Hematology, Abstract #248*, 2002.

Shaughnessy et al., "Global gene expression analysis shows loss of C-MYC and IL-6 receptor gene mRNA after exposure of myeloma to thalidomide and IMiD," Abstract # 2485, *The American Society of Hematology*, Dec. 1-5, 2000.

Shire et al., "TNF-α inhibitors and rheumatoid arthritis," *Exp. Opin. Ther. Patents*, 1998, 8 (5):531-544.

Sorbbera et al., "CC-5013. Treatment of multiple myeloma. Treatment of Melanoma. Treatment of myelodysplastic syndrome. Angiogenesis inhibitor. TNF-α production inhibitor," *Drugs of the Future*, 2003, 28(5):425-431.

Streetly et al., "Thalidomide analogue CC-4047 is effective in the treatment of patients with relapsed and refractory multiple myeloma (MM) and induces T-cell activation and IL-12 production," Abstract # 367, *International Multiple Myeloma Workshop*, May 23-27, 2003.

Streetly et al., "Changes in neutrophil phenotype following the administration of CC-4047 (Actimid) to patients with multiple myeloma," Abstract # 2543, *American Society of Hematology*, Dec. 6-9, 2003.

Streetly et al, "An update of the use and outcomes of the new immunomodulatory agent CC-4047 (Actimid) in patients with relapsed/refractory myeloma," Abstract #829, *American Society of Hematology*, Dec. 6-9, 2003.

Teo et al., "A phase I, single-blind, placebo-controlled, ascending single oral dose, safety, tolerability and pharmacokinetic study of CDC-501, a novel immunomodulatory—oncologic agent, in healthy male subjects with a comparison of fed and fasted," *Clinical Pharmacology and Therapeutics*, 2002, 71 (2)93.

Teo et al., "Chiral inversion of the second generation IMiD™ CC-4047 (ACTIMID™) in human plasma and phosphate-buffered saline," *Chirality*, 2003, 15:348-351.

Thertulien et al., "Hybrid MEL/DT PACE autotransplant regimen for Multiple Myeloma (MM)—safety and efficacy data in pilot study of 15 patients," *Blood Abstract # 2869, American Society of Hematology*, Dec. 7-11, 2001.

Tohnya et al., "A phase I study of oral CC-5013 (lenalidomide, Revlimid™), a thalidomide derivative, in patients with refractory metastatic cancer," *Clinical Prostate Cancer*, 2004, 2:241-243.

Tricot et al., "Angiochemotherapy (ACT) for multiple myloma (MM) with DT-PACE results in a high response rate, but in contrast to tandem transplants with melphalan does not affect durable disease control," *Blood, Abstract # 3531, American Society of Hematology*, Dec. 7-11, 2001.

Tsenova et at, "Use of IMiD3, a thalidomide analog, as an adjunct to therapy for experimental tuberculous meningitis," *Antimicrobial Agents and Chemotherapy*, 2002, 46 (6)1887-1895.

Weber, "Lenalidomide (CC-5013, Revlimid™) and other ImiDs," Abstract # PL5.02, *International Multiple Myeloma Workshop*, Apr. 10-14, 2005.

Weber et al., "A multicenter, randomized, parallel-group, double-blind, placebo-controlled study of lenalidomide plus dexamethasone versus dexamethasone alone in previously treated subjects with multiple myeloma," Abstract # PO.738, *International Multiple Myeloma Workshop*, Apr. 10-14, 2005.

Ye et al., "Novel IMiD drugs enhance expansion and regulate differentiation of human cord blood CD34+ cells with cytokines," *Blood, Abstract #4099, American Society of Hematology*, Dec. 6-10, 2002.

Zangari et al., "Risk factors for deep vein thrombosis (DVT) in a large group of myeloma patients (Pts) treated with thalidomide (Thal): The Arkansas Experience," *Blood, Abstract # 681, American Society of Hematology*, Dec. 7-11, 2001.

Zangari et al, "Revimid 25 mg (REV 25) × 20 versus 50 mg (REV 50) × 10 q 28 days with bridging of 5 mg × 10 versus 10 mg × 5 as post-transplant salvage therapy for multiple myeloma (MM)," *Blood, Abstract # 1642, American Society of Hematology*, Dec. 6-9, 2003.

Zeldis et al., "Potential new therapeutics for Waldenstrom's macroglobulinemia," *Seminars in Oncology*, 2003, 30 (2):275-281.

Zhang et al., "CC-5079, a novel microtubule and TNF-α inhibitor with anti-angiogenic and antimetastasis activity," Abstract # B012, *International Conference on Molecular Targets and Cancer Therapeutics*, Nov. 17-21, 2003.

Anderson, "The Role of Immunomodulatory Drugs in Multiple Myeloma," *Seminars in Hematology*. vol. 40, No. 4, Suppl 4, 2003: pp. 23-32.

Weber, "Thalidomide and Its Derivatives: New Promise for Multiple Myeloma," *Cancer Control*, vol. 10, No. 5, 375-383, 2003.

U.S. Appl. No. 60/499,723, filed Sep. 4, 2003, Markian.
U.S. Appl. No. 60/372,348, filed Apr. 12, 2002, Hariri et al.
U.S. Appl. No. 10/732,867, filed Dec. 9, 2003, D'Amato et al.
U.S. Appl. No. 09/545,654, filed Apr. 10, 2000, D'Amato.
U.S. Appl. No. 09/287,377, filed Apr. 7, 1999, D'Amato.

Carstensen, 1995, *Drug Stability: Principles & Practice*, 2$^{nd}$. ed., Marcel Dekker, New York, NY pp. 379-380.

Corral et al., 1999, "Immunomodulation by thalidomide and thalidomide analogues," Ann. Rheum. Dis. 58(Suppl 1):1107-113.

Craig et al., 1967, "Potential anticancer agents. III. 2-phthalimidoaldehydes and derivatives," Potential Anticancer Agents III 10:1071-1073.

D'Amato et al., 2001, "Mechanism of action of thalidomide and 3-aminothalidomide in multiple myeloma," Semin. Oncol. 28:597-601.

D'Amato et al., 1994, "Thalidomide is an Inhibitor of Angiogenesis", Proc. Natl. Acad. Sci. 91:4082-4085.

De et al., 1976, "Hansch analysis for some antineoplastic glutarimides," J. Indian Chem. Soc. I.III: 825-826.

De et al., 1976, "Possible antineoplastic agents: Ill. Synthesis of 6-alkyl-2-[4'-methoxyphthalimido] and 6-alkyl-3-[3'-4'-dimethoxyphenyl] glutarimides," J. Indian Chem. Soc. I.III:1122-1125.

Dredge et al., 2002, "Novel thalidomide analogues display antiangiogenic activity independently of immunomodulatory effects," Br. J. Cancer 87(10):1166-1172.

Folkman et al., 1983, "Angiogenesis inhibition and tumor regression caused by heparin or a heparin fragment in the presence of cortisone," Science 221(4612):719-725.

Gershbein, 1991, "The thalidomide analog, EM 12, enhances 1,2-dimethylhydrazine-induction of rat colon adenocarcinomas," Cancer Letters 60: 129-133.

Grabstald et al., 1965, "Clinical experiences with thalidomide in patients with cancer," Clinical Pharmacology and Therapeutics 6:298-302.

Lentzsch et al., 2003, "Immunomodulatory analogs of thalidomide inhibit growth of Hs Sultan cells and angiogenesis in vivo," Leukemia 17(1):41-44.

Lentzsch et al., 2002, "S-3-amino-phthalimido-glutarimide inhibits angiogenesis and growth of B-cell neoplasias in mice", Cancer Research 62:2300-2305.

Miyachi et al., 1997, "Novel biological response modifiers: phthalimides with tumor necrosis factor-alpha production-regulating activity," J. Med. Chem. 40:2858-2865.

Muller et al., 1999, "Amino-substituted thalidomide analogs: potent inhibitors of TNF-alpha production," Bioorg. Med. Chem. Lett. 9(11):1625-1630.

Muller et al., 1998, "Thalidomide analogs and PDE4 inhibition," Bioorg. Med. Chem. Lett. 8(19):2669-2674.

Muller et al., 1996, "Structural modifications of thalidomide produce analogs with enhanced tumor necrosis factor inhibitory activity," J. Med. Chem. 39(17):3238-3240.

Olson et al., 1965, "Thalidomide (N-phthaloylglutamimide) in the treatment of advanced cancer," Clinical Pharmacology and Therapeutics 6(3):292-297.

Penichet et al., 2001, "Antibody-cytokine fusion proteins for the therapy of cancer," J. Immunol. Methods 248(1-2):91-101.

*Physician's Desk Reference*, 2002, 56$^{th}$ ed., pp. 1755-1760.

Attal et al., 2004, "Maintenance treatment with thalidomide after autologous transplantation for myeloma: First analysis of a prospective randomized study of the Intergroupe Francophone du Myelome (IFM 99 02)," Am. Soc. Hematol. 46th Ann. Meeting Dec. 4-7, 2004, San Diego, CA Abstract #535.

Bernardeschi et al., 2003, J. Exp. Clin. Cancer Res. 22(4):129-133.

Dimopoulos et al., 2004, "Primary treatment with puilsed melphalan, dexamethasone, thalidomide (MDT) for symptomatic patients with multiple myeloma ÿ75 years of age," Am. Soc. Hematol. 46th Ann. Meeting Dec. 4-7, 2004, San Diego, CA Abstract #1482.

Rajkumar et al., 2004, "Thalidomide plus dexamethasone versus dexamethasone alone in newly diagnosed multiple myeloma (E1A00): Results of a phase III trial coordinated by the Eastern Cooperative Oncology Group," Am. Soc. Hematol. 46th Ann. Meeting Dec. 4-7, 2004, San Diego, CA Abstract #205.

Bach, 1963, "Thalidomide in Cancer Chemotherapy," The Lancet, No. 1271, p. 71.

Bach, 1963, "Studies on the Possible Anti-Neoplastic Effect of Thalidomide," Acta Pathologica Et Microbiologica Scandinavica 59:491-499.

Chaundhry, 1966, Cancer Research, "Effect of Prednisolone and Thalidomide on Induced Submandibular Gland Tumors in Hamster," 26(part 1)1884-86.

DiPaolo, 1963, "Effect of Thalidomide on a Variety of Transplantable Tumors," Cancer Chemotherapy Reports No. 29, p. 99-102.

DiPaolo, 1963, "In vitro Test Systems for Cancer Chemotherapy, II. Correlation of in vitro Inhibition of Dehydrogenase and Growth with in vivo Inhibition of Ehrlich Asoites Tumor," Proceedings of the Society for Experimental Biology & Medicine, 114:384-387.

Mauad, 1963, "Clinical Improvements Obtained in Advanced Caner Patients with Treatment with Thalidomide Associated with Hormones," Anais Paulistas de Medicina e Cirurgia 86:13-40.

Roe and Mitchley, 1963, "Thalidomide and Neoplasia" Nature 200:1016-1017.

Liu et al., "Phase I study of CC-5013 (Revimid), a thalidomide derivative, in patients with refractory metastatic cancer," American Society of Clinical Oncology, Abstract #927, 2003.

Zangari et al., "Results of phase I study of CC-5013 for the treatment of multiple myeloma (MM) patients who relapse after high dose chemotherapy (HDCT)," American Society of Hematology, Abstract #3226, 2001.

Zeldis et al., "Update on the evolution of the IMiD™," International Society for Biological Therapy of Cancer, Oral Abstract, 2003.

Anderson, "Moving disease biology from the laboratory to the clinic," Seminars in Oncology, 2002 29:17-20.

Barlogie et al., "Total Therapy II (TTII) for newly diagnosed multiple myeloma (MM): preliminary data on feasibility and efficacy in the first 231 enrolled patients; comparison with predecessor trial total therapy I ((TTI) (N=231)," Blood, Abstract # 2857, Dec. 7-11, 2001, American Society of Hematology.

Barlogie et al., "High-dose therapy immunomodulatory drugs in multiple myeloma," Seminars in Oncology, 2002, 29 (6):26-33.

Barlogie et al., "Introduction: Thalidomide and the IMiDs in multiple myeloma," Seminars in Hematology, 2003, 40 (4):1-2.

Barlogie, "Thalidomide and CC-5013 in Multiple Myeloma: The University of Arkansas experience," Seminars in Hematology, 2003, 40 (4):33-38.

Bartlett et al., "The evolution of thalidomide and its IMiD derivatives as anticancer agents," Nature Reviews Cancer, 2004, 4 (4): 1 -9.

Bartlett et al., "Phase I study to determine the safety, tolerability and immunostimulatory activity of thalidomide analogue CC-5013 in patients with metastatic malignant melanoma and other advanced cancers," British Journal of Cancer, 2004, 90:955-961.

Battegay, "Angiogenesis: mechanistic insights, neovascular diseases, and therapeutic prospects," J. Mol. Med., 1995, 73:333-346.

Baz et al., "Doxil (D), vincristine (V), reduced frequency dexamethasone (d) and revlimid (R) (DVd-R) results in a high response rate in patients with refractory multiple myeloma (RMM)," Blood, Abstract # 2559, American Society of Hematology, Dec. 10-13, 2005.

Brennen et al., "Thalidomide and analogues: current proposed mechanisms and therapeutic usage," Clinical Prostate Cancer, 2004, 3 (1):54-61.

Celgene Corporation, "Celgene advances immunomodulatory drug (IMiD™) clinical program," Press Release, Feb. 2000.

Celgene Corporation, "Additional clinical data presented on Revimid™ in myelodysplastic sydromes at the American Society of Hematology 45th annual meeting," Press Release, Dec. 2003.

Dalgleish, et al., "New thalidomide analogues; anti-cancer, anti-angiogenic and immunostimulatory," British Journal of Cancer, 2001, 85 (1)25.

Dalgleish et al., "Thalidomide analogues CC-50I3 and CC-4047 induce T cell activation and IL-12 production in patients with both solid tumours and relapsed and refractory multiple myeloma," British Journal of Cancer, 2003, 88(Suppl I), S25-S54.

Davies et al., "Thalidomide (Thal) and immunomodulatory derivatives (IMiDs) augment natural killer (NK) cell cytotoxicity in multiple myeloma(MM))," Abstract # 3617, American Society of Hematology, Dec. 1-5, 2000.

Davies et al., "Thalidomide (Thal) and immunomodulatory derivatives (IMiDs) augment natural killer (NK) cell cytotoxicity in multiple myeloma ~MM)," Abstract # P222, VIIIth International Myelomi Workshop, May 4-8, 2001.

Dibbs et al., "Thalidomide and thalidomide analogs suppress TNFÿ secretion by myocytes," Abstract # 1284, Circulation, 1998.

Dimopoulos et al., "Results of thalidomide and IMIDs in multiple myeloma,", Abstract # P12.1.4, International Multiple Myeloma Workshop, May 23-27, 2003.

Dimopoulos et al., "Treatment of plasma cell dyscrasias with thalidomide and its derivatives," Journal of Clinical Oncology, Dec. 1, 2003, 21 (23)4444-4454.

Dimopoulos et al., "Study of lenalidomide plus dexamethasone versus dexamethasone alone in relapsed or refractory multiple myeloma (MM): Results of a phase 3 Study (MM-010),", Abstract # 6, American Society of Hematology, Dec. 10-13, 2005.

Dredge et al., A costimulatory thalidomide analog enhances the partial anti-tumor immunity of an autologous vaccination in a model of colorectal cancer, Abstract # 491, American Association for Cancer Research, Apr. 6-10, 2002.

Dredge et al., "Adjuvants and the promotion of Th 1-type cytokines in tumour immunotherapy," Cancer Immunol. Immunother., 2002, 51:521-531.

Dredge et al., "Immunological effects of thalidomide and its chemical and functional analogs," Critical Reviews in Immunology, 2002, 22 (5&6):425-437.

Dredge et al., "Protective antitumor immunity induced by a costimulatory thalidomide analog in conjunction with whole tumor cell vaccination is mediated by increased Th 1-type immunity1," The Journal of Immunology, 2002, 168:4914-4919.

Dredge et al., "Recent developments in antiangiogenic therapy," Expert Opin. Biol. Ther., 2002, 2 (8):953-966.

Dredge et al., "Angiogenesis inhibitors in cancer therapy," Current Opinion in Investigational Drugs, 2003, 4 (6):667-674.

Dredge et al., "Thalidomide analogs as emerging anti-cancer drugs," Anti-Cancer Drugs, 2003, 14:331-335.

Fickentscher et al., "Stereochemical properties and teratogenic activity of some tetrahydrophthalimides," Molecular Pharmacology, 1976, 13:133-141.

Figg et al., "Inhibition of angiogenesis: treatment options for patients with metastatic prostate cancer," Investigational New Drugs, 2002, 20(2):183-194.

Galustian et al., "Thalidomide-derived immunomodulatory drugs as therapeutic agents," Expert Opin. Biol. Ther., 2004,4(12):1-8.

Glaspy et al., "The potential role of thalidomide and thalidomide analogs in melanoma," Clinical Advances in Hematology & Oncology, 2004, 1-7.

Gupta et al., "Adherence of multiple myeloma cells to bone marrow stromal cells upregulates vascular endothelial growth factor secretion: therapeutic applications," Leukemia, 2001, 15:1950-1961.

Hayashi et al., "Mechanisms whereby immunomodulatory analogs of thalidomide augment autologous NK cell anti-myeloma immunity," Blood, Abstract #3219, Dec. 6-10, 2002, American Society of Hematology.

Helm et al., "Comparative teratological investigation of compounds of structurally and pharmacologically related to thalidomide," Arzneimittel Forschung/Drug Research, 1981, 31 (1)941-949.

Hernandez-ILlizaliturr et al., "Addition of immunomodulatory drugs CC5013 or CC4047 to rituximab enhances anti-tumor activity in a severe combined immunodeficiency (SCID) mouse lymphoma model," Abstract # 235, American Society of Hematology, Dec. 6-9, 2003.

Hideshima et al., "Thalidomide and its analogs overcome drug resistance of human multiple myeloma cells to conventional therapy," Blood, 2000, 96:2943-2950, American Society of Hematology.

Hideshima et al., "Thalidomide (Thal) and its analogs overcome drug resistance of human multiple myeloma (MM) cells to conventional therapy," Abstract 1313, American Society of Hematology, Dec. 1-5, 2000.

Hunt et al., "Markers of endothelial and haemostatic activation in the use of CC-4047, a structural analogue of thalidamide, in relapsed myeloma," Blood, Abstract # 3216, Dec. 6-10, 2002, American Society of Hematology.

Hussein et al., "Doxil (D), vincristine (V), reduced frequency dexamethasone (d) and Revlimid (DVd-R) a phase I/II trial in advanced relapsed/refractory multiple myeloma (Rmm) patients," Blood, Abstract #208, American Society of Hematology, Dec. 4-7, 2004.

Hwu et al., "Thalidomide and its analogues in the treatment of metastatic melanoma," Chemotherapy Foundation Symposium, Abstract #44, 2002.

Kyle, "Current therapy of multiple myeloma," Internal Medicine, 2002, 41 (3)175-180.

Kyle et al., "Multiple myeloma," New England Journal of Medicine, 2004, 351:1860-1873.

LeBlanc et al., "Immunomodulatory drug costimulates T cells via the B7-CD28 pathway," Blood, 2004, 103:1787-1790, American Society of Hematology.

Lentzsch et al., "In vivo activity of thalidomide and immunomodulatory drugs against multiple myeloma," VIIIth International Myeloma Workshop, Abstract #P225, May 4-8, 2001.

Lentzsch et al., "Immunomodulatory derivative of thalidomide (IMiD CC-4047) determine the lineage commitment of hematopoietic progenitors by down regulation of GATA-1 and modulation of cytokine secretion," Abstract # 3073, American Society of Hematology, Dec. 6-9, 2003.

Lentzsch et al., "Immunomodulatory derivative of thalidomide (IMiD CC-4047) down regulates CAAT/enhancer-binding protein ÿ(C/EBP ÿ) in multiple myeloma (MM)," Abstract # 3456, American Society of Hematology, Dec. 6-9, 2003.

Luzzio et al., "Thalidomide analogues: derivatives of an orphan drug with diverse biological activity," Expert Opin. Ther. Patents, 2004, 14 (2):215-229.

Man et al., "ÿ—Fluoro-substituted thalidomide analogues," Bioorganic & Medicinal Chemistry Letters 13, 2003, 3415-3417.

Marriott et al., "Immunotherapeutic and antitumour potential of thalidomide analogues," Expert Opin. Biol. Ther., 2001, 1 (4):1-8.

Marriott et al., "New thalidomide analogues; anti-cancer, anti-angiogenic and immunostimulatory," British Journal of Cancer, 85:25, Jul. 6, 2001.

Marriott et al., "Thalidomide and its analogues have distinct and opposing effects on TNF-$\alpha$ and TNFR2 during co-stimulation of both CD4+ and CD8+ T cells," Clin. Exp. Immunol., 2002, 130:75-84.

Marriott et al., "A novel subclass of thalidomide analogue with anti-solid tumor activity in which caspase-dependent apoptosis is associated with altered expression of bcl-2 family proteins 1," Cancer Research, 2003, 63:593-599.

Marriott et al., "Thalidomide derived immunomodulatory drugs (IMiDs) as potential therapeutic agents," Current DrugTargets—Immune, Endocrine & Metabolic Disorders, 2003, 3:181-186.

Masellis et al., "Changes in gene expression in bone marrow mesenchymal progenitor cells as a consequence of IMiD therapy in multiple myeloma patients," Blood, Abstract # 1548, Dec. 7-11, 2001, American Society of Hematology.

McCarty, "Thalidomide may impede cell migration in primates by down-regulating integrin $\gamma$-chains: potential therapeutic utility in solid malignancies, proliferative retinopathy, inflammatory disorders, neointimal hyperplasia, and osteoporosis," Medical Hypotheses, 1997, 49:123-131.

Mitsiades et al., "Apoptic signaling induced by immunomodulatory thalidomide analogs (Imids) in human multiple myeloma cells: therapeutic implications," Abstract # 3224, Dec. 7-11, 2001, American Society of Hematology.

Mitsiades et al., "Apoptic signaling induced by immunomodulatory thalidomide analogs in human multiple myeloma cells: therapeutic implications," Blood, 2002, 99:4525-4530, American Society of Hematology.

Mitsiades et al., "CC-5013 Celgene," Current Opinion in Investigational Drugs, 2004, 5 (6):635-647.

Moutouh et al., "Novel immunomodulatory drugs (IMiDs®): A potential, new therapy for $\gamma$-hemoglobinopathies.", Abstract # 3740, American Society of Hematology, Dec. 4-7, 2004.

Patten et al., "The early use of the serum free light chain assay in patients with relapsed refractory myeloma receiving treatment with a thalidomide analogue (CC-4047)," Abstract # 1640, American Society of Hematology, Dec. 6-9, 2003.

Payvandi et al., "Effects of a thalidomide analog on binding activity of transcription factors and cell cycle progression of multiple myeloma cell lines," Blood, Abstract #2487, Dec. 1-5, 2000, American Society of Hematology.

Payvandi et al., "The thalidomide analogs IMiDs enhance expression of CD69 stimulatory receptor on natural killer cells," Abstract # 1793, American Association for Cancer Research, Mar. 24-28, 2001.

Payvandi et al., "Thaliomide analogs IMiDs inhibit expression of cyclooxygenase-2 in multiple myeloma cell line and LPS stimulated PBMCs," Blood, Abstract # 2689, Dec. 7-11, 2001, American Society of Hematology.

Payvandi et al., "Thalidomide and IMiDS inhibit microvessel formation from human arterial rings in the absence of human liver microsomes," Blood, Abstract # 5046, Dec. 6-10, 2002, American Society of Hematology.

Payvandi et al., "CC-5013 inhibits the expression of adhesion molecules ICAM-1 and CD44 and prevents metastasis of B16 F10 mouse melanoma cells in an animal model," American Society of Clinical Oncology, Abstract # 992, 2003.

Payvandi et al., "Immunomodulatory drugs inhibit expression of cyclooxygenase-2 from TNF-α, IL-1α, and LPS-stimulated human PBMC in a partially IL-10-dependent manner," Cellular Immunology, 2004, 81-88.

Raje et al., "Combination of the mTOR inhibitor rapamycin and CC-5013 has synergistic activity in multiple myeloma," Blood, Dec. 15, 2004, 104 (13)4188-4193.

Rajkumar et al., "Combination therapy with lenalidomide plus dexamethasone (Rev/Dex) for newly diagnosed myeloma," Blood, Dec. 15, 2005, 106 (13)4050-4053.

Richardson et al., "A Phase 1 study of oral CC5013, an immunomodulatory thalidomide (Thal) derivative, in patients with relapsed and refractory multiple myeloma (MM)," Blood, Abstract #3225, Dec. 7-11, 2001, American Society of Hematology.

Richardson et al., "Immunomodulatory drug CC-5013 overcomes drug resistance and is well tolerated in patients with relapsed multiple myeloma," Blood, 2002 100:3063-3067, American Society of Hematology.

Richardson et al., "A multi-center, randomized, phase 2 study to evaluate the efficacy and safety of 2 CDC-5013 dose regimens when used alone or in combination with dexamethasone (Dex) for the treatment of relapsed or refractory multiple myeloma (MM)," Blood, Abstract # 825, American Society of Hematology, Dec. 6-9, 2003.

Richardson et al., "Immunomodulatory analogs of thalidomide: an emerging new therapy in myeloma," Journal of Clinical Oncology, 2004, 22(16) 3212-3214.

Richardson et al., "A multicenter, single-arm, open-label study to evaluate the efficacy and safety of single-agent lenalidomide in patients with relapsed and refractory multiple myeloma; preliminary results," 10th International Myeloma Workshop, Apr. 10-14, 2005.

Richardson et al., "Novel biological therapies for the treatment of multiple myeloma," Best Practice & Research Clinical Haerfiatology, 2005, 18 (4):619-634.

Richardson et al., "A phase 1 trial of lenalidomide (REVLIMID®) with bortezomib (VELCADE® ) in relapsed and refractory multiple myeloma," Blood, Abstract # 365, American Society of Hematology, Dec. 10-13, 2005.

Schafer et al., "Enhancement of cytokine production and AP-1 transcriptional activity in T cells by thalidomide-related immunomodulatory drugs," Journal of Pharmacology and Experimental Therapeutics, 2003, 305(3)1222-1232.

Schey et al., "A phase I study of an immunomodulatory thalidomide analog, CC-4047, in relapsed or refractory multiple myeloma," Journal of Clinical Oncology, 2004, 22 (16):1-8.

Schey et al., "A phase I study of an immunomodulatory thalidomide analogue (CC4047) in relapse/refractory multiple myeloma," International Society for Experimental Hematology, Abstract #248, 2002.

Shaughnessy et al., "Global gene expression analysis shows loss of C-MYC and IL-6 receptor gene mRNA after exposure of myeloma to thalidomide and IMiD," Abstract # 2485, The American Society of Hematology, Dec. 1-5, 2000.

Shire et al., "TNF-β inhibitors and rheumatoid arthritis," Exp. Opin. Ther. Patents, 1998, 8 (5):531-544.

Sorbera et al., "CC-5013. Treatment of multiple myeloma. Treatment of Melanoma. Treatment of myelodysplastic syndrome. Angiogenesis inhibitor. TNF-β production inhibitor," Drugs of the Future, 2003, 28(5):425-431.

Streetly et al., "Thalidomide analogue CC-4047 is effective in the treatment of patients with relapsed and refractory multiple myeloma (MM) and induces T-cell activation and IL-12 production," Abstract # 367, International Multiple Myeloma Workshop, May 23-27, 2003.

Streetly et al., "Changes in neutrophil phenotype following the administration of CC-4047 (Actimid) to patients with multiple myeloma," Abstract # 2543, American Society of Hematology, Dec. 6-9, 2003.

Streetly et al., "An update of the use and outcomes of the new immunomodulatory agent CC-4047 (Actimid) in patients with relapsed/refractory myeloma," Abstract #829, American Society of Hematology, Dec. 6-9, 2003.

Teo et al., "A phase I, single-blind, placebo-controlled, ascending single oral dose, safety, tolerability and pharmacokinetic study of CDC-501, a novel immunomodulatory- oncologic agent, in healthy male subjects with a comparison of fed and fasted," Clinical Pharmacology and Therapeutics, 2002, 71 (2)93.

Teo et al., "Chiral inversion of the second generation IMiD™ CC-4047 (ACTIMID™ ) in human plasma and phosphate-buffered saline," Chirality, 2003, 15:348-351.

Thertulien et al., "Hybrid MEL/DT PACE autotransplant regimen for Multiple Myeloma (MM)—safety and efficacy data in pilot study of 15 patients," Blood, Abstract # 2869, American Society of Hematology, Dec. 7-11, 2001.

Tohnya et al., "A phase I study of oral CC-50I3 (lenalidomide, Revlimid™), a thalidomide derivative, in patients with refractory metastatic cancer," Clinical Prostate Cancer, 2004, 2:241-243.

Tricot et al., "Angiochemotherapy (ACT) for multiple myloma (MM) with DT-PACE results in a high response rate, but in contrast to tandem transplants with melphalan does not affect durable disease control," Blood, Abstract # 3531, American Society of Hematology, Dec. 7-11, 2001.

Tsenova et al., "Use of IMiD3, a thalidomide analog, as an adjunct to therapy for experimental tuberculous meningitis," Antimicrobial Agents and Chemotherapy, 2002, 46 (6)1887-1895.

Weber, "Lenalidomide (CC-5013, Revlimid™) and other ImiDs," Abstract # PL5.02, International Multiple Myeloma Workshop, Apr. 10-14; 2005.

Weber et al., "A multicenter, randomized, parallel-group, double-blind, placebo-controlled study of lenalidomide plus dexamethasone versus dexamethasone alone in previously treated subjects with multiple myeloma," Abstract # PO.738, International Multiple Myeloma Workshop, Apr. 10-14, 2005.

Ye et al., "Novel IMiD drugs enhance expansion and regulate differentiation of human cord blood CD34+ cells with cytokines," Blood, Abstract #4099, American Society of Hematology, Dec. 6-10, 2002.

Zangari et al., "Risk factors for deep vein thrombosis (DVT) in a large group of myeloma patients (Pts) treated with thalidomide (Thal): The Arkansas Experience," Blood, Abstract # 681, American Society of Hematology, Dec. 7-11, 2001.

Zangari et al., "Revimid 25 mg (REV 25) × 20 versus 50 mg (REV 50) × 10 q 28 days with bridging of 5 mg × 10 versus 10 mg × 5 as post-transplant salvage therapy for multiple myeloma (MM)," Blood, Abstract # 1642, American Society of Hematology, Dec. 6-9, 2003.

Zeldis et al., "Potential new therapeutics for Waldenstrom's macroglobulinemia," Seminars in Oncology, 2003, 30 (2):275-281.

Zhang et al., "CC-5079, a novel microtubule and TNF-a inhibitor with anti-angiogenic and antimetastasis activity," Abstract # B012, International Conference on Molecular Targets and Cancer Therapeutics, Nov. 17-21, 2003.

Anderson, "The Role of Immunomodulatory Drugs in Multiple Myeloma," Seminars in Hematology, vol. 40, No. 4, Suppl 4, 2003: pp. 23-32.

Weber, "Thalidomide and Its Derivatives: New Promise for Multiple Myeloma," Cancer Control, vol. 10, No. 5, 375-383, 2003.

Patt, Yehuda A.; Hassan, Manal M.; Lozano, Richard D.; Ellis, Lee M.; Peterson, J. Andrew; Waugh, Kimberly A.; Durable Clinical Response of Refractory Hepatocellular Carcinoma to Orally Administered Thalidomide. American Journal of Clinical Oncology, 2000.

Richardson, Paul; Hideshima, Teru; Anderson, Kenneth; Thalidomide: The Revival of a Drug with Therapeutic Promise in the Treatment of Cancer; Principles & Practice of Oncology, vol. 15, No. 2, 2001.

Thomas, Melodie; DOSS, Deborah, Thalidomide Nursing Roundtable Update, Monograph, Sep. 2002.

Richardson, Paul; Hideshima, Teru; Anderson, Kenneth; Thalidomide: Emerging Role in Cancer Medicine; Annual Review of Medicine, 2002.

Berenson, J.R.; Bergsagel, P. L.; Munshi, N.; Initiation and Maintenance of Multiple Myeloma; Seminars in Hematology, vol. 36, No. 1, Supp. 3, Jan. 1999, pp. 9-13.

Gollob, J.A.; Schinpper, C.P.; Orsini, E.; Murphy, E.; Daley, J.F.; Lazo, S.B.; Frank. D.A.; Characterization of a Novel Subset of CD8 T Cells That Expands in patients Receiving Interleukin-12, 02, Am. Soc. For Clin. Investigation, Inc., vol. 102, No. 3, Aug. 1998, pp. 561-575.

Cavanagh, L.L.; Barnetson, R.S.; Basten, A.; Halliday, G.M.; Dendritic Epidermal T-Cell Involvement in Induction of CD8+

T-Cell-Mediated Immunity Against an Ultraviolet Radiation-Induced Skin Tumor Int. J. Cancer: 70, 98-105, 1997.

Thomas, D.A., Aguayo, A., Estey, E., Albitar, M., O'Brien, S., Giles, F.J., Beran, M., Cortes, J., Zeldis, J., Keating, M.J., Barlogie, B., Kantarjian, H.M., Thalidomide as anti-angiogenesis therapy (rx) in refractory or relapsed leukemia. Abstract #2269, American Society of Hematology, Dec. 3-7, 1999.

Barlogie, B., Desikan, R., Munshi, N., Siegel, D., Mehta, J., Singhal, S., Anaissie, E., Single Course D.T. Pace Anti-Angiochemotherapy Effects CR in Plasma Cell Leukemia and Fulminant Multiple Myeloma (MM). Abstract #4180. American Society of Hematology, Dec. 4-9, 1998.

Hideshima, T., Chauhan, D., Shima, Y., Noopur, R., Davies, F.E., Tai, Y., Treon, S.P., Lin, B.K., Schlossman, R.L., Richardson, P.G., Gupta, D., Muller, G.W., Stirling, D.I., Anderson, K.C., Thalidome (THAL) and its Analogs Overcome Drug Resistance of Human Multiple Myeloma (MM) Cells to Conventional Therapy. Abstract #1313. American Society of Hematology, Dec. 1-5, 2000.

Payvandi, F., Wu, L., Gupta, D., Hideshima, T., Haley, M., Muller, G., Chen, R., Anderson, K.C., Stirling, D., Effects of a Thalidomide Analog on Binding Activity of Transcription Factors and Cell Cycle Progression of Multiple Myeloma Cell Lines. Abstract #2487. American Society of Hematology, Dec. 1-5, 2000.

Davies, F.E., Raje, N., Hideshima, T., Lentzsch, S., Young, G., Tai, Y., Lin, B.K., Podar, K., Chauhan, D., Treon, S.P., Gupta, D., Mitsiades, C., Mitsiades, N., Hayashi, T., Richardson, P.G., Schlossman, R.L., Muller, G.W., Stirling, D. I., Anderson, K.C., Thalidomide (THAL) and Immunomodulatory Derivatives (IMiDS) Augment Natural Killer (NK) Cell Cytotocicity in Multiple Myeloma (MM). Abstract #3617. American Society of Hematology, Dec. 1-5, 2000.

Hideshima, T., Chauhan, D., Castro, A., Hayashi, T., Mitsiades, C., Mitsiades, N., Akiyama, M., Richardson, P.G., Schlossman, R.L., Adams, J., Anderson, K.C., NF-γB as a Therapeutic Target in Multiple Myeloma (MM). Abstract #1581. American Society of Hematology, Dec. 7-11, 2001.

Lentsch, S., Rogers, M., LeBlanc, R., Birsner, A., Shah, J., Anderson K., D'Amato R., 3-Amino-Phthalimido-Glutarimide (S-3APG) Inhibits Angiogenesis and Growth in Drug Resistant Multiple Myeloma (MM) in vivo. Abstract #1976, American Society of Hematology, Dec. 7-11, 2001.

Park, Y., Kim, S.A., Kim, C.J., Chung, J.H., Mechanism of the Effect of Thalidomide on Human Multiple Myeloma Cells. Abstract #2685. American Society of Clinical Oncology, May 12-17, 2001.

Payvandi, F., Wu, L., Haley M., Gupta, D., Zhang, L., Schafer, P., Muller, G.W., Chen, R., Anderson, K.C., Stirling, D., Thalidomide Analogs IMiDS Inhibit Expression of Cyclooxygenase-2 in Multiple Myeloma Cell Line and LPS Stimulated PBMCs. Abstract #2689. American Society of Hematology, Dec. 7-11, 2001.

Mitsiades, N., Mitsiades, C., Poulaki, V., Akiyama, M., Tai, Y., Lin, B., Hayashi, T., Catley, L., Hideshima, T., Chauhan, D., Treon, S.P., Anderson, K.C., Apoptotic Signaling Induced by Immunomodulatory Thalidomide Analogs (Imids) in Human Multiple Myeloma Cells; Therapeutic Implications. Abstract #3224. American Society of Hematology, Dec. 7-11, 2001.

"Celgene drug promises activity in solid tumors," *Marketletter*, Jun. 18, 2001.

Marriott et al., "Thalidomide analogue CDC-501 is safe and well tolerated by patients with end stage cancer and shows evidence of clinical responses and extensive immune activation," *Br. J. Cancer*, 2002, 86(Supp. I):Abst 6.4.

Kast, R.E., "Evidence of a mechanism by which etanercept increased TNF-alpha in multiple myeloma: New insights into the biology of TNF-alpha giving new treatment opportunities—the role of burproion," *Leukemia Research*, 2005, 29:1459-1463.

Tsimberidou, A. et al., "Pilot study of recombinant human soluble tumor necrosis factor (TNF) receptor (p75) fusion protein (TNFR:Fc;Enbrel) in patients with refractory multiple myeloma: increase in plasma TNFα levels during treatment," *Leukemia Research*, 2003, 27:375-380.

Dimopoulos, et al., "Long-term follow-up on overall survival from the MM-009 and MM-010 phase III trials of lenalidomide plus dexamethasone in patients with relapsed or refractory multiple myeloma," *Leukemia*, 2009, 1-6.

Hideshima, T., et al., "A review of lenalidomide in combination with dexathasone for the treatment of multiple myeloma," *Therapeutics and Clinical Risk Management*, 2008, 4(1):129-136.

Wang, M., et al., "Lenalidomide plus dexamethasone is more effective than dexamethasone alone in patients with relapsed or refractory multiple myeloma regardless of prior thalidomide exposure," *Blood*, 2008, 112(12):4445-4451.

Gandhi, A., et al., "Dexamethasone Synergizes with Lenalidomide to Inhibit Multiple Myeloma Tumor Growth, But Reduces Lenalidomide-Induced Immunomodulation of T and NK Cell Function," *Current Cancer Drug Targets*, 2010, 10(1):1-13.

Gay, F. et al., "Lenalidomide plus dexamethasone versus thalidomide plus dexamethasone in newly diagnosed multiple myeloma: a comparative analysis of 411 patients," *Blood*, 2010, 115(97):1343-150.

Notification letter dated Aug. 30, 2010 from Natco Pharma Limited to Celgene Corporation re: Notification purusant to § 505(j)(2)(B) of the Federal Food, Drug and Cosmetic Act.

Complaint for Patent Infringement filed on Oct. 8, 2010 by Celgene Corporation in the U.S. District Court, District of New Jersey against Natco Pharma Limited.

Answer to Complaint filed on Nov. 18, 2010 by Natco Pharma Limited in the U.S. District Court, District of New Jersey.

Grosshans, E. and Illy, G., "Thalidomide Therapy for Inflammatory Dermatoses," *International Journal of Dermatology*, 1984, 23(9):598-602.

Krenn, M. et al., "Improvements in Solubility and Stability of Thalidomide upon Complexation with Hydropropyl-β-Cyclodextrin," *Journal of Pharmaceutical Sciences*, 1992, 81(7):685-689.

Schmahl, H. J. et al., "Pharmacokinetics of the Teratogenic and Nonteratogenic Thalidomide Analogs EM 12 and Supidimide in the Rat and Marmoset Monkey", in *Pharmacokinetics in Teratogenesis*, CRC Press, 1987, vol. I, Ch. 12, pp. 181-192.

Schumacher, H. et al., "The Teratogenic Activity of a Thalidomide Analogue, $EM_{12}$, in Rabbits, Rats, and Monkeys," *Teratology*, 1971, 5:233-240.

Smith, R. et al.. "Studies on the Relationship Between the Chemical Structure and Embryotoxic Activity of Thalidomide and Related Compounds," in *A Symposium on Embryopathic Activity of Drugs*, J. & A. Churchill Ltd., 1965, Session 6, pp. 194-209.

Sheskin, J. and Sagher, F., "Trials with Thalidomide Derivatives in Leprosy Reactions," *Leprosy Review*, 1968, 39(4):203-205.

Sheskin, J., "Study with Nine Thalidomide Derivatives in the Lepra Reaction," *Pharmacology and Therapeutics*, 1978,17:82-84.

Raje, N. and Anderson, K., "thalidomide and immunomodulatory drugs as cancer therapy," *Current Opinions in Oncology*, 2002, 14:635-640.

Kumar, S. et al., "Thalidomide as an anti-cancer agent," *J. Cell. Mod. Med.*, 2002, 6(2):160-174.

Singhal, S. and Mehta, J., "Thalidomide in Cancer," *BioDrugs*, 2001, 15(3):163-172.

List, A., "New Approaches to the Treatment of Myelodysplasia," *The Oncologist*, 2002, 7(suppl. I):39-49.

Kurzrock, R., "Myelodysplastic syndrome overview,"*Seminars in Hematology* (Abstract only), 2002, 39(3)suppl. 2):18-25 *Abstract only*.

Goerner, et al., "Morbidity and mortality of chronic GVHD after hematopoictic stem cell transplantation from HLA-identical siblings for patients with aplastic or refractory anemias," *Biology of Blood and Marrow Transplantation* (Abstract only), 2002, 8(1):47-56.

Thomas, D., "Pilot studies of Thalidomide in Acute Myelogenous Leukemia, Myelodysplastic Syndromes, and Myeloproliferative Disorders,"*Seminars in Hematology*, 2000, 37(I)(suppl. 3):26-34.

Zorat. F. et al., "The clinical and biological effects of thalidomide in patients with myelodysplastic syndromes," *British Journal of Haematology*, 2001, 115:881-894.

Official Action dated Feb. 10, 2009 in JP Application No. 2004-545192. (*English translation provided*).

Teramura, M., Men-ekiyokusei Ryouhou, *Current Therapy*, 2000, 18(5):140-144 (in Japanese).

Kon-nichi no Chiryou Shishin, 1997 [Pocket Edition], Igaku Shoin, 1997, 513-514 (in Japanese).

Okamoto, T., Kotsuzuiikeisei Shoukougun to Men-eki Ijo, Bessatsu Nihon Rinsho. Syndrome Series for each area, No. 22, Blood Syndromes III, Nihon Rlnshou, 213-216 (in Japanese), (Oct. 1998).

Merck Manual, 17$^{th}$ ed. Japanese version, 1999, 951-952.

Notice of Allowance from U.S. Appl. No. 11/096,155 dated Jan. 12, 2010.

Rajkumar et al., "Combination therapy with thalidomide plus dexameerhasone for newly diagnosed multiple myeloma," *American Society of Hematology*, 43$^{rd}$ Annual Meeting, Dec. 7-11, 2001, Abstract #3525.

Scheffler et al., "Safety and pharmacokinetics of CDC-501, a novel immunomodulatory-oncologic agent, after single then multiple, oral 100 mg twice daily dOSeS," *American Society for Clinical Pharmacology and Therapeutics*, Mar. 24-27, 2002, Abstract #WPIII-63.

Meregalli et al., "High-dose dexamethasone as first line therapy of multiple myeloma?", *Recenti Progressi in Medicina*, 1998, 89(1):18-20.

Official Action in corresponding Canadian Application No. 2,476,983, (dated Aug. 21, 2009).

Liu et al, "Phase I study of CC-5013 (Revimid). a thalidomide derivative, in patients with refractory metastatic cancer," *American Society of Clinical Oncology*, Abstract #927, 2003.

Zeldis et al. "Update on the evolution of the IMID™," *International Society for Biological Therapy of Cancer, Oral Abstract*, 2003.

Patt, Yehuda A.; Hassan, Manal) M.; Lozano, Richard D.; Ellis, Lee M.; Peterson, J. Andrew; Waugh, Kimberly A.; *Durable Clinical Response of Refractory Hepatocellular Carcinoma to Orally Administered Thalidomide*, American Journal of Clinical Oncology, 2000.

Richardson, Paul; Hideshima, Terur, Anderson, Kenneth; *Thalidomide: The Revival of a Drug with Therapeutic Promise in the Treatment of Cancer*, Principles & Practice of Oncology, vol. 15, No. 2, 2001.

Thomas, Melodie; Doss, Deborah, *Thalidomide Nursing Roundtable Update*, Monograph, Sep. 2002.

Richardson, Paul; Hidesibma, Teru; Anderson, Kenneth; *Thalidomide: Emerging Role in Cancer Medicine*; Annual Review of Medicine, 2002.

Berenson, J.R.; Bergsagel, P. L.; Munshi, N., *Initiation and Maintenance of Multiple Myeloma*; Seminars in Hematology, vol. 36 No. 1, Supp.3, Jan. 1999, pp. 9-13.

Gollob, J.A.; Schinpper, C.P.; Orsini, E.; Murphy, E.; Daley, J.F.; Lazo, S.B.; Frank. D.A.; *Characterization of a Novel Subset of CD8 T Cells That Expands in patients Receiving interleukin-12*, 02, Am. Soc. For Clin. Investigation, Inc., vol. 102. No. 3 Aug. 1998, pp. 561-575.

Cavanagh, L.L.; Barnetson, R.S.; Basten, A.; Halliday, G.M.; *Dendritic Epidermal T-Cell Involvement in Induction of CD8+ T-Cell-Mediated Immunity Against an Ultraviolet Radiation-Induced Skin Tumor* Int. J. Cancer: 70, 98-105, 1997.

Thomas, D.A., Aguayo, A., Estey, E., Albitar, M., O'Brien, S., Giles, F. J., Beran, M., Cortes, J., Zeldis, I., Keating, M.J., Barlogie, B., Kantarjian, H.M., Thalidomide as anti-angiogenesis therapy (rx) in refractory or relapsed leukemia. Abstract #2269, American Society of Hematology, Dec. 3-7, 1999.

Barlogie, B., Desikan, R., Munshi, N., Siegel., D., Meheas, J., Singhal, S., Anaissie, E., Single Course D.T. Pace Anti-Angiochernotherapy Effects CR in Plasma Cell Leukemia and Fulminent Multiple Myeloma (MM), Abstract #4180. American Society of Hematology, Dec. 1-9, 1998.

Davies, F. E., Raje, N., Hideshima, T., Lentzsch, S., Young G., Tai, Y., Lin, B.K., Podar, K., Chauhan, D., Treon, S.P., Gupta, D., Mitsiades, C., Mitsiades, N., Hayashi, T., Richardson, P.G., Schlossman, R.L., Muller, G.W., Stirling, D.L., Anderson, K.C., Thalldomide (THAL) and Immunomodulatory Derivatives (IMiDS) Augment Natural Killer (NK) Cell Cytotocixity in Multiple Myeloma (MM). Abstract #3617. American Society of Hematology, Dec. 1-5, 2000.

Hideshima, T., Chauhan, D., Castro, A., Hayashi, T Mitsiades, C., Mitsiades, N., Akiyama, M., Richardson. P.G., Schlossman, R.L., Adams, J., Anderson, K.C., NF-KB as a Therapeutic Target in Multiple Myeloma (MM). Abstract # 1581. American Society of Hematology. Dec. 7-11, 2001.

Lentsch, S.. Rogers, M., LeBlanc, R., Birsner, A., Shah, J., Anderson K., D'Amato R., 3-Amino-Phthalimido-Glutarimidde (S-3APG) Inhibits Angiogenesis and Growth in Drug Resistant Multiple Myeloma (MM) in vivo. Abstract # 1976. American Society of Hematology, Dec. 7-11, 2001.

Park, Y., Kim. S.A., Kim, C.J., Chung, J.H., Mechanism of the Effect of Thalidomide on Human Multiple Myeloma Cells. Abstract #2685. American Society of Clinical Oncology, May 12-17, 2001.

Payvandi, F., Wu, I., Haley M., Gupta, D., Zhang, L., Schafer, P., Muller, G.W., Chen, R., Anderson, K.C., Stirling, D., Thalidomide Analogs IMiDS Inhibit Expression of Cyclooxygenase-2 in Multiple Myeloma Cell Line and LPS Stimulated PBMCs. Abstract #2689. American Society of Hemmology, Dec. 7-11, 2001.

Mitslades, N., Mitslades, C., Poulaki, V., Akiyama, M., Tai, Y., Lin, B., Hayashi, T., Cati.F.Y, L., Hideshima, T., Chauhan, D., Treon, S.P., Anderson, K.C., Apoptotic Signaling Induced By Immunomodulatory Thalidomide Analogs (Imids) in Human Multiple Myeloma Cells; Therapeutic Implications, Abstract #3224. American Society of Hematology, Dec. 7-11, 2001.

Richardson, P.G., Schlossman, R.L., Hideshima, T., Davies, F., LeBlanc, R., Catley, L., Doss, D., Kelly, K.A., McKenney, M., Mechlowicz, J., Freeman, A., DeOcampo, Il, R., Rich, R., Ryoo, J., Chauhan, D., Munshi, N., Weller, E., Zeldis, J., Anderson, K.C., A Phase 1 Study of Oral CC5013, an Immunomodulatory Thalidomide (Thal) Derivative, in Patients With Relapsed and Refractory Multiple Myeloma (MM). Abstract #3225. American Society of Hematology, Dec. 7-11, 2001.

Zangari, M. Tricot, G., Zeldis, J., Eddlemon, P., Saghafifar, F., Barlogie, B., Results of Phase 1 Study of CC5013, for the Treatment of Multiple Myeloma (MM) Patients Who Replase After High Dose Chemotherapy (HDCT). Abstract #3226. American Society of Hematology, Dec. 7-11, 2001.

Richardson, P. et al, "Thalidomide in multiple myeloma," *Biomed Pharmacother*, 2002, 56:115-28.

Swartz, G. et al., "Pre-clinical evaluation of ENMD-0995: A thalidomide analog with activity against multiple myeloma and solid tumors," *Cell and Tumor Biology*, 2002, 43:181-182, Abstract# 910.

Mazucco, R., "Angiogenesis and Anti-angiogenesis Therapeutics." *IDrugs*, 2002, 5(4): 320-322.

Worker, C., "JP Morgan Hambreclu & Quist—20$^{th}$ Annual Healthcare Conference," *IDrugs*, 5(2):113-116, (2002).

Treston, A. et al., "Pre-Clinical Evaluation of a Thalidomide Analog with Activity Against Multiple Myeloma and Solid Tumors— ENMD-0995 (S-(-)-3-(3-amino-phthalimido)-glutarimide)," *Blood*, 100(11):816a, Abstract #3225.

Mazucco, R. and Williams, L., "Imnamotherapy, chemoprovention and angiogenesis," *IDrugs*, 2002, 5(5):408-411.

Fernandes, P., "Anti-Cancer Drug Discovery and Development Summit," *IDrugs*, 2002, 5(8):757-764.

Notice of Opposition to EP 1 505 973 filed by Synthon B.V. on Nov. 30, 2010.

Notice of Opposition to EP 1 505 973 filed by Strawman Limited on Dec. 1, 2010.

Samson, D. et al., "Infusion of Vincristine and Doxorubicin with Oral Dexamethasone as First-Line Therapy for Multiple Myeloma," *The Lancet*, 1989, 334(8668):882-885.

Barlogie, B. et al., "Effective Treatment of Advanced Multiple Myeloma Refractory to Alkylating Agents," *N. Engl. J. Med.*, 1984, 310(21):1353-1356.

Dimopoulos, M. et al., "Thalidomide and dexamethasone combination for refractory multiple myeloma," *Annals of Oncology*, 2001, 12:991-995.

Zangari, M., et al., "Thrombogenic activity of doxonibicin in myeloma patients receiving thalidomide: implications for therapy," *Blood*, 2002, 100:1168-1171.

List, A. et al., "High Erythropoietic Remitting Activity of the Immunomodulatory Thalidomide Analog, CC5013, in Patients with Myelodysplastic Syndrome (MDS)," Abstract #353, *Blood*, 2002, 100(11):96a.

Mufti, G. et al., "Myclodysplastic Syndrome," *American Society of Hematology*, 2003, pp. 176-199.

Extracts from drug databases: retrieved from http://www.nextbio.com/b/search/ov/IMiD3%20cpd on Nov. 26, 2010 and http://pubchem.ncbi.nlm.nih.gov/summary/summary.cgi?cid=216326 on Nov. 26, 2010.

* cited by examiner

Effects of Revimid™ and Thalidomide on MM Cell Proliferation

METHODS FOR TREATMENT OF MULTIPLE MYELOMA USING 3-(4-AMINO-1-OXO-1,3-DIHYDRO-ISOINDOL-2-YL)-PIPERIDINE-2,6-DIONE

This application claims the benefit of U.S. provisional application No. 60/380,842, filed May 17, 2002, and No. 60/424,600, filed Nov. 6, 2002, the entireties of which are incorporated herein by reference.

1. FIELD OF THE INVENTION

This invention relates to methods of treating, preventing and/or managing specific cancers, and other diseases including, but not limited to, those associated with, or characterized by, undesired angiogenesis, by the administration of one or more immunomodulatory compounds alone or in combination with other therapeutics. In particular, the invention encompasses the use of specific combinations, or "cocktails," of drugs and other therapy, e.g., radiation to treat these specific cancers, including those refractory to conventional therapy. The invention also relates to pharmaceutical compositions and dosing regimens.

2. BACKGROUND OF THE INVENTION

2.1 Pathobiology of Cancer and Other Diseases

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples includes cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, bFGF).

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to: diabetic retinopathy; retinopathy of prematurity; corneal graft rejection; neovascular glaucoma; retrolental fibroplasia; and proliferative vitreoretinopathy.

Accordingly, compounds that can control angiogenesis or inhibit the production of certain cytokines, including TNF-α, may be useful in the treatment and prevention of various diseases and conditions.

2.2 Methods of Treating Cancer

Current cancer therapy may involve surgery, chemotherapy, hormonal therapy and/or radiation treatment to eradicate neoplastic cells in a patient (see, for example, Stockdale, 1998, *Medicine, vol.* 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A majority of cancer chemotherapeutics act by inhibiting DNA synthesis, either directly, or indirectly by inhibiting the biosynthesis of deoxyribonucleotide triphosphate precursors, to prevent DNA replication and concomitant cell division. Gilman et al., *Goodman and Gilman's: The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove refractory to standard chemotherapeutic treatment protocols.

Other diseases or conditions associated with, or characterized by, undesired angiogenesis are also difficult to treat. However, some compounds such as protamine, hepain and steroids have been proposed to be useful in the treatment of certain specific diseases. Taylor et al., *Nature* 297:307 (1982);

Folkman et al., *Science* 221:719 (1983); and U.S. Pat. Nos. 5,001,116 and 4,994,443. Thalidomide and certain derivatives of it have also been proposed for the treatment of such diseases and conditions. U.S. Pat. Nos. 5,593,990, 5,629,327, 5,712,291, 6,071,948 and 6,114,355 to D'Amato.

Still, there is a significant need for safe and effective methods of treating, preventing and managing cancer and other diseases and conditions, particularly for diseases that are refractory to standard treatments, such as surgery, radiation therapy, chemotherapy and hormonal therapy, while reducing or avoiding the toxicities and/or side effects associated with the conventional therapies.

2.3 IMIDS™

A number of studies have been conducted with the aim of providing compounds that can safely and effectively be used to treat diseases associated with abnormal production of TNF-α See, e.g., Marriott, J. B., et al., *Expert Opin. Biol. Ther.* 1(4):1-8 (2001); G. W. Muller, et al., Journal of Medicinal Chemistry 39(17): 3238-3240 (1996); and G. W. Muller, et al, Bioorganic & Medicinal Chemistry Letters 8: 2669-2674 (1998). Some studies have focused on a group of compounds selected for their capacity to potently inhibit TNF-α production by LPS stimulated PBMC. L. G. Corral, et al., Ann. Rheum. Dis. 58:(Suppl I) 1107-1113 (1999). These compounds, which are referred to as IMiDS™ (Celgene Corporation) or Immunomodulatory Drugs, show not only potent inhibition of TNF-α but also marked inhibition of LPS induced monocyte IL1β and IL12 production. LPS induced IL6 is also inhibited by immunomodulatory compounds, albeit partially. These compounds are potent stimulators of LPS induced IL10. Id. Particular examples of IMiD™s include, but are not limited to, the substituted 2-(2,6-dioxopiperidin-3-yl) phthalimides and substituted 2-(2,6-dioxopiperidin-3-yl)-1-oxoisoindoles described in U.S. Pat. Nos. 6,281,230 and 6,316,471, both to G. W. Muller, et al.

3. SUMMARY OF THE INVENTION

This invention encompasses methods of treating and preventing certain types of cancer, including primary and metastatic cancer, as well as cancers that are refractory or resistant to conventional chemotherapy. The methods comprise administering to a patient in need of such treatment or prevention a therapeutically or prophylactically effective amount of an immunomodulatory compound, or a pharmaceutically acceptable salt, solvate, hydrate, stereoisomer, clathrate, or prodrug thereof. The invention also encompasses methods of managing certain cancers (e.g., preventing or prolonging their recurrence, or lengthening the time of remission) which comprise administering to a patient in need of such management a prophylactically effective amount of an immunomodulatory compound of the invention, or a pharmaceutically acceptable salt, solvate, hydrate, stereoisomer, clathrate, or prodrug thereof.

In particular methods of the invention, an immunomodulatory compound is administered in combination with a therapy conventionally used to treat, prevent or manage cancer. Examples of such conventional therapies include, but are not limited to, surgery, chemotherapy, radiation therapy, hormonal therapy, biological therapy and immunotherapy.

This invention also encompasses methods of treating, managing or preventing diseases and disorders other than cancer that are associated with, or characterized by, undesired angiogenesis, which comprise administering to a patient in need of such treatment, management or prevention a therapeutically or prophylactically effective amount of an immunomodulatory compound, or a pharmaceutically acceptable salt, solvate, hydrate, stereoisomer, clathrate, or prodrug thereof.

In other methods of the invention, an immunomodulatory compound is administered in combination with a therapy conventionally used to treat, prevent or manage diseases or disorders associated with, or characterized by, undesired angiogenesis. Examples of such conventional therapies include, but are not limited to, surgery, chemotherapy, radiation therapy, hormonal therapy, biological therapy and immunotherapy.

This invention encompasses pharmaceutical compositions, single unit dosage forms, dosing regimens and kits which comprise an immunomodulatory compound, or a pharmaceutically acceptable salt, solvate, hydrate, stereoisomer, clathrate, or prodrug thereof, and a second, or additional, active agent. Second active agents include specific combinations, or "cocktails," of drugs.

4. BRIEF DESCRIPTION OF FIGURE

FIG. 1 shows a comparison of the effects of 3-(4-amino-1-oxo-1,3-dihydro-isoindol-2-yl)-piperidine-2,6-dione (Revimid™) and thalidomide in inhibiting the proliferation of multiple myeloma (MM) cell lines in an in vitro study. The uptake of [$^3$H]-thymidine by different MM cell lines (MM. 1S, Hs Sultan, U266 and RPMI-8226) was measured as an indicator of the cell proliferation.

5. DETAILED DESCRIPTION OF THE INVENTION

A first embodiment of the invention encompasses methods of treating, managing, or preventing cancer which comprises administering to a patient in need of such treatment or prevention a therapeutically or prophylactically effective amount of an immunomodulatory compound of the invention, or a pharmaceutically acceptable salt, solvate, hydrate, stereoisomer, clathrate, or prodrug thereof.

In particular methods encompassed by this embodiment, the immunomodulatory compound is administered in combination with another drug ("second active agent") or method of treating, managing, or preventing cancer. Second active agents include small molecules and large molecules (e.g., proteins and antibodies), examples of which are provided herein, as well as stem cells. Methods, or therapies, that can be used in combination with the administration of the immunomodulatory compound include, but are not limited to, surgery, blood transfusions, immunotherapy, biological therapy, radiation therapy, and other non-drug based therapies presently used to treat, prevent or manage cancer.

Another embodiment of the invention encompasses methods of treating, managing or preventing diseases and disorders other than cancer that are characterized by undesired angiogenesis. These methods comprise the administration of a therapeutically or prophylactically effective amount of an immunomodulatory compound, or a pharmaceutically acceptable salt, solvate, hydrate, stereoisomer, clathrate, or prodrug thereof.

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle).

In particular methods encompassed by this embodiment, the immunomodulatory compound is administer in combination with a second active agent or method of treating, managing, or preventing the disease or condition. Second active agents include small molecules and large molecules (e.g., proteins and antibodies), examples of which are provided herein, as well as stem cells. Methods, or therapies, that can be used in combination with the administration of the immunomodulatory compound include, but are not limited to, surgery, blood transfusions, immunotherapy, biological therapy, radiation therapy, and other non-drug based therapies presently used to treat, prevent or manage disease and conditions associated with, or characterized by, undesired angiogenesis.

The invention also encompasses pharmaceutical compositions (e.g., single unit dosage forms) that can be used in methods disclosed herein. Particular pharmaceutical compositions comprise an immunomodulatory compound of the invention, or a pharmaceutically acceptable salt, solvate, hydrate, stereoisomer, clathrate, or prodrug thereof, and a second active agent.

5.1 Immunomodulatory Compounds

Compounds used in the invention include immunomodulatory compounds that are racemic, stereomerically enriched or stereomerically pure, and pharmaceutically acceptable salts, solvates, hydrates, stereoisomers, clathrates, and prodrugs thereof. Preferred compounds used in the invention are small organic molecules having a molecular weight less than about 1,000 g/mol, and are not proteins, peptides, oligonucleotides, oligosaccharides or other macromolecules.

As used herein and unless otherwise indicated, the terms "immunomodulatory compounds" and "IMiDs™" (Celgene Corporation) encompasses small organic molecules that markedly inhibit TNF-α, LPS induced monocyte IL1β and IL12, and partially inhibit IL6 production. Specific immunomodulatory compounds are discussed below.

TNF-α is an inflammatory cytokine produced by macrophages and monocytes during acute inflammation. TNF-α is responsible for a diverse range of signaling events within cells. TNF-α may play a pathological role in cancer. Without being limited by theory, one of the biological effects exerted by the immunomodulatory compounds of the invention is the reduction of synthesis of TNF-α. Immunomodulatory compounds of the invention enhance the degradation of TNF-αmRNA.

Further, without being limited by theory, immunomodulatory compounds used in the invention may also be potent co-stimulators of T cells and increase cell proliferation dramatically in a dose dependent manner. Immunomodulatory compounds of the invention may also have a greater co-stimulatory effect on the CD8+ T cell subset than on the CD4+ T cell subset. In addition, the compounds preferably have anti-inflammatory properties, and efficiently co-stimulate T cells.

Specific examples of immunomodulatory compounds of the invention, include, but are not limited to, cyano and carboxy derivatives of substituted styrenes such as those disclosed in U.S. Pat. No. 5,929,117; 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. No. 5,874,448; the tetra substituted 2-(2,6-dioxopiperdin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide and EM-12), including, but not limited to, those disclosed in U.S. Pat. No. 5,635,517; and a class of non-polypeptide cyclic amides disclosed in U.S. Pat. Nos. 5,698,579 and 5,877,200; analogs and derivatives of thalidomide, including hydrolysis products, metabolites, derivatives and precursors of thalidomide, such as those described in U.S. Pat. Nos. 5,593,990, 5,629,327, and 6,071,948 to D'Amato; aminothalidomide, as well as analogs, hydrolysis products, metabolites, derivatives and precursors of aminothalidomide, and substituted 2-(2,6-dioxopiperidin-3-yl) phthalimides and substituted 2-(2,6-dioxopiperidin-3-yl)-1-oxoisoindoles such as those described in U.S. Pat. Nos. 6,281,230 and 6,316,471; isoindole-imide compounds such as those described in U.S. patent application Ser. No. 09/972,487 filed on Oct. 5, 2001, U.S. patent application Ser. No. 10/032,286 filed on Dec. 21, 2001, and International Application No. PCT/US01/50401 (International Publication No. WO 02/059106). The entireties of each of the patents and patent applications identified herein are incorporated herein by reference. Immunomodulatory compounds of the invention do not include thalidomide.

Other specific immunomodulatory compounds of the invention include, but are not limited to, 1-oxo- and 1,3 dioxo-2-(2,6-dioxopiperidin-3-yl) isoindolines substituted with amino in the benzo ring as described in U.S. Pat. No. 5,635,517 which is incorporated herein by reference. These compounds have the structure I:

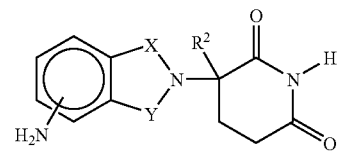

in which one of X and Y is C=O, the other of X and Y is C=O or CH$_2$, and R$^2$ is hydrogen or lower alkyl, in particular methyl. Specific immunomodulatory compounds include, but are not limited to:

1-oxo-2-(2,6-dioxopiperidin-3-yl)-4-aminoisoindoline;

1-oxo-2-(2,6-dioxopiperidin-3-yl)-5-aminoisoindoline;

1-oxo-2-(2,6-dioxopiperidin-3-yl)-6-aminoisoindoline;

1-oxo-2-(2,6-dioxopiperidin-3-yl)-7-aminoisoindoline;

1,3-dioxo-2-(2,6-dioxopiperidin-3-yl)-4-aminoisoindoline; and 1,3-dioxo-2-(2,6-dioxopiperidin-3-yl)-5-aminoisoindoline.

Other specific immunomodulatory compounds of the invention belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Compounds representative of this class are of the formulas:

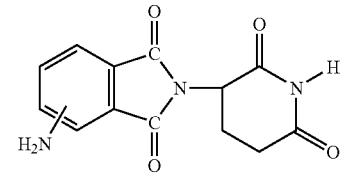

-continued

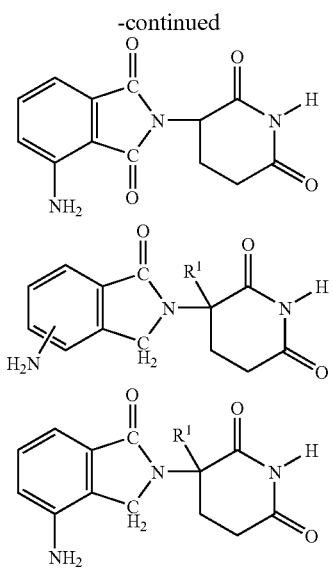

wherein R¹ is hydrogen or methyl. In a separate embodiment, the invention encompasses the use of enantiomerically pure forms (e.g. optically pure (R) or (S) enantiomers) of these compounds.

Still other specific immunomodulatory compounds of the invention belong to a class of isoindole-imides disclosed in U.S. patent application Ser. Nos. 10/032,286 and 09/972,487, and International Application No. PCT/US01/50401 (International Publication No. WO 02/059106), each of which are incorporated herein by reference. Representative compounds are of formula II:

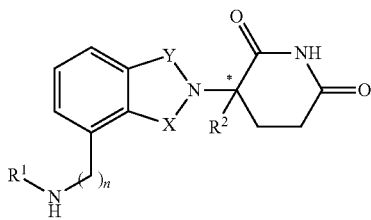

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(O)NHR^3$, $C(S)NHR^3$, $C(O)NR^3R^{3'}$, $C(S)NR^3R^{3'}$ or $(C_1-C_8)$alkyl-$O(CO)R^5$;

$R^2$ is H, F, benzyl, $(C_1-C_8)$alkyl, $(C_2-C_8)$alkenyl, or $(C_2-C_8)$alkynyl;

$R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl$(C_1-C_6)$heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;

$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$(C_1-C_6)$heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O$—$R^5$ or the $R^6$ groups can join to form a heterocycloalkyl group;

n is 0 or 1; and

* represents a chiral-carbon center.

In specific compounds of formula II, when n is 0 then $R^1$ is $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(S)NHR^3$, or $(C_1-C_8)$alkyl $O(CO)R^5$;

$R^2$ is H or $(C_1-C_8)$alkyl; and $R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_5-C_8)$alkyl-$N(R^6)_2$; $(C_0-C_8)$alkyl-NH—$C(O)O$—$R^5$; $(C_1-C_8)$alkyl-$OR^5$, $(C_1-C_8)$alkyl-$C(O)OR^5$, $(C_1-C_8)$alkyl-$O(CO)R^5$, or $C(O)OR^5$; and the other variables have the same definitions.

In other specific compounds of formula II, $R^2$ is H or $(C_1-C_4)$alkyl.

In other specific compounds of formula II, $R^1$ is $(C_1-C_8)$alkyl or benzyl.

In other specific compounds of formula II, $R^1$ is H, $(C_1-C_8)$alkyl, benzyl, $CH_2OCH_3$, $CH_2CH_2OCH_3$, or

In another embodiment of the compounds of formula II, $R^1$ is

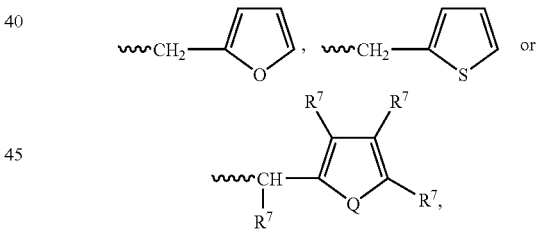

wherein Q is O or S, and each occurrence of $R^7$ is independently H, $(C_1-C_8)$alkyl, benzyl, $CH_2OCH_3$, or $CH_2CH_2OCH_3$.

In other specific compounds of formula II, $R^1$ is $C(O)R^3$.

In other specific compounds of formula II, $R^3$ is $(C_0-C_4)$alkyl-$(C_2-C_5)$heteroaryl, $(C_1-C_5)$alkyl, aryl, or $(C_0-C_4)$alkyl-$OR^5$.

In other specific compounds of formula II, heteroaryl is pyridyl, furyl, or thienyl.

In other specific compounds of formula II, $R^1$ is $C(O)OR^4$.

In other specific compounds of formula II, the H of C(O) NHC(O) can be replaced with $(C_1-C_4)$alkyl, aryl, or benzyl.

Still other specific immunomodulatory compounds of the invention belong to a class of isoindole-imides disclosed in U.S. patent application Ser. No. 09/781,179, International Publication No. WO 98/54170, and U.S. Pat. No. 6,395,754, each of which are incorporated herein by reference. Representative compounds are of formula III:

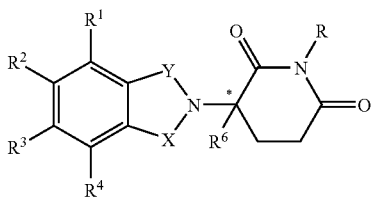

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

R is H or $CH_2OCOR'$;

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or $-NHR^5$ and the remaining of $R^1$, $R^2$, $R^3$, or $R^4$ are hydrogen;

$R^5$ is hydrogen or alkyl of 1 to 8 carbons $R^6$ hydrogen, alkyl of 1 to 8 carbon atoms, benzo, chloro, or fluoro;

R' is $R^7$—$CHR^{10}$—$N(R^8R^9)$;

$R^7$ is m-phenylene or p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2[X]X_1CH_2CH_2$— in which $[X]X_1$ is —O—, —S—, or —NH—;

$R^{10}$ is hydrogen, alkyl of to 8 carbon atoms, or phenyl; and

* represents a chiral-carbon center.

The most preferred immunomodulatory compounds of the invention are 4-(amino)-2-(2,6-dioxo(3-piperidyl))-isoindoline-1,3-dione and 3-(4-amino-1-oxo-1,3-dihydro-isoindol-2-yl)-piperidine-2,6-dione. The compounds can be obtained via standard, synthetic methods (see e.g., U.S. Pat. No. 5,635,517, incorporated herein by reference). The compounds are available from Celgene Corporation, Warren, N.J. 4-(Amino)-2-(2,6-dioxo(3-piperidyl))-isoindoline-1,3-dione (ACTIMID™) has the following chemical structure:

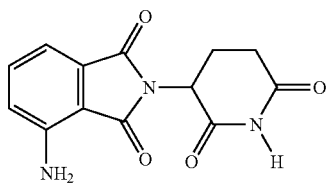

The compound 3-(4-amino-1-oxo-1,3-dihydro-isoindol-2-yl)-piperidine-2,6-dione (REVIMID™) has the following chemical structure:

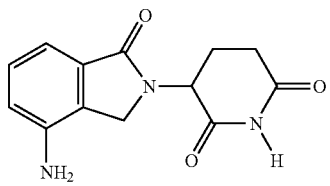

Compounds of the invention can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of immunomodulatory compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds of the invention that comprise —NO, —$NO_2$, —ONO, or —$ONO_2$ moieties. Prodrugs can typically be prepared using well-known methods, such as those described in 1 *Burger's Medicinal Chemistry and Drug Discovery*, 172-178, 949-982 (Manfred E. Wolff ed., 5th ed. 1995), and *Design of Prodrugs* (H. Bundgaard ed., Elsevier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

Various immunomodulatory compounds of the invention contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular immunomodulatory compounds of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N.Y., 1962); and Wilen, S. H., *Tables of Resolving Agents and Optical Resolutions* p. 268 (E. L. Eliel, Ed., Univ. of Notre Dame Press, Notre Dame, Ind., 1972).

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.2 Second Active Agents

Immunomodulatory compounds can be combined with other pharmacologically active compounds ("second active agents") in methods and compositions of the invention. It is believed that certain combinations work synergistically in the treatment of particular types of cancer and certain diseases and conditions associated with, or characterized by, undesired angiogenesis. Immunomodulatory compounds can also work to alleviate adverse effects associated with certain second active agents, and some second active agents can be used to alleviate adverse effects associated with immunomodulatory compounds.

One or more second active ingredients or agents can be used in the methods and compositions of the invention together with an immunomodulatory compound. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful in this invention include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions of the invention include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

This invention encompasses the use of native, naturally occurring, and recombinant proteins. The invention further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with compounds of the invention include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. Compounds of the invention can also be combined with, or used in combination with, anti-TNF-α antibodies.

Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits of the invention. See, e.g., Emens, L. A., et al., *Curr. Opinion Mol. Ther.* 3(1):77-84 (2001).

In one embodiment of the invention, the large molecule active agent reduces, eliminates, or prevents an adverse effect associated with the administration of an immunomodulatory compound. Depending on the particular immunomodulatory compound and the disease or disorder begin treated, adverse effects can include, but are not limited to, drowsiness and somnolence, dizziness and orthostatic hypotension, neutropenia, infections that result from neutropenia, increased HIV-viral load, bradycardia, Stevens-Johnson Syndrome and toxic epidermal necrolysis, and seizures (e.g., grand mal convulsions). A specific adverse effect is neutropenia.

Second active agents that are small molecules can also be used to alleviate adverse effects associated with the administration of an immunomodulatory compound. However, like some large molecules, many are believed to be capable of providing a synergistic effect when administered with (e.g., before, after or simultaneously) an immunomodulatory compound. Examples of small molecule second active agents include, but are not limited to, anti-cancer agents, antibiotics, immunosuppressive agents, and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®), imiquimod; immunostimulant peptides;

insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

5.3 Methods of Treatments and Prevention

Methods of this invention encompass methods of treating, preventing and/or managing various types of cancer and diseases and disorders associated with, or characterized by, undesired angiogenesis. As used herein, unless otherwise specified, the term "treating" refers to the administration of a compound of the invention or other additional active agent after the onset of symptoms of the particular disease or disorder. As used herein, unless otherwise specified, the term "preventing" refers to the administration prior to the onset of symptoms, particularly to patients at risk of cancer, and other diseases and disorders associated with, or characterized by, undesired angiogenesis. The term "prevention" includes the inhibition of a symptom of the particular disease or disorder. Patients with familial history of cancer and diseases and disorders associated with, or characterized by, undesired angiogenesis are preferred candidates for preventive regimens. As used herein and unless otherwise indicated, the term "managing" encompasses preventing the recurrence of the particular disease or disorder in a patient who had suffered from it, and/or lengthening the time a patient who had suffered from the disease or disorder remains in remission.

As used herein, the term "cancer" includes, but is not limited to, solid tumors and blood born tumors. The term "cancer" refers to disease of skin tissues, organs, blood, and vessels, including, but not limited to, cancers of the bladder, bone or blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, sceloderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage 1V non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation; in particular, refractory to thalidomide.

As used herein to refer to diseases and conditions other than cancer, the terms "diseases or disorders associated with, or characterized by, undesired angiogenesis," "diseases or disorders associated with undesired angiogenesis," and "diseases or disorders characterized by undesired angiogenesis" refer to diseases, disorders and conditions that are caused, mediated or attended by undesired, unwanted or uncontrolled angiogenesis, including, but not limited to, inflammatory diseases, autoimmune diseases, genetic diseases, allergic diseases, bacterial diseases, ocular neovascular diseases, choroidal neovascular diseases, and retina neovascular diseases.

Examples of such diseases or disorders associated with undesired angiogenesis include, but are not limited to, diabetic retinopathy, retinopathy of prematurity, corneal graft rejection, neovascular glaucoma, retrolental fibroplasia, proliferative vitreoretinopathy, trachoma, myopia, optic pits, epidemnic keratoconjunctivitis, atopic keratitis, superior limbic keratitis, pterygium keratitis sicca, sjogrens, acne rosacea, phylectenulosis, syphilis, lipid degeneration, bacterial ulcer, fungal ulcer, Herpes simplex infection, Herpes zoster infection, protozoan infection, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, sickle cell anemia, sarcoid, pseudoxanthoma elasticum, Pagets disease, vein occlusion, artery occlusion, carotid obstructive disease, chronic uveitis, chronic vitritis, Lyme's disease, Eales disease, Bechets disease, retinitis, choroiditis, presumed ocular histoplasmosis, Bests disease, Stargarts disease, pars planitis, chronic retinal detachment, hyperviscosity syndromes, toxoplasmosis, rubeosis, sarcodisis, sclerosis, soriatis, psoriasis, primary sclerosing cholangitis, proctitis, primary biliary srosis, idiopathic pulmonary fibrosis, and alcoholic hepatitis.

In specific embodiments of the invention, diseases or disorders associated with undesired angiogenesis do not include congestive heart failure, cardiomyopathy, pulmonary edema, endotoxin-mediated septic shock, acute viral myocarditis, cardiac allograft rejection, myocardial infarction, HIV, hepatitis, adult respiratory distress syndrome, bone-resorption disease, chronic obstructive pulmonary diseases, chronic pulmonary inflammatory disease, dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft rejection, rheumatoid spondylitis, osteoporosis, Crohn's disease, ulcerative colitis, inflammatory-bowel disease, multiple sclerosis, systemic lupus erythrematosus, erythema nodosum leprosum in leprosy, radiation damage, asthma, hyperoxic alveolar injury, malaria, mycobacterial infection, and opportunistic infections resulting from HIV.

This invention encompasses methods of treating patients who have been previously treated for cancer or diseases or disorders associated with, or characterized by, undesired angiogenesis, but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer and diseases and disorders characterized by undesired angiogenesis have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer and other diseases or disorders.

Methods encompassed by this invention comprise administering one or more immunomodulatory compound of the invention, or a pharmaceutically acceptable salt, solvate, hydrate, stereoisomer, clathrate, or prodrug thereof, to a patient (e.g., a human) suffering, or likely to suffer, from cancer or a disease or disorder mediated by undesired angiogenesis.

In one embodiment of the invention, an immunomodulatory compound of the invention can be administered orally and in single or divided daily doses in an amount of from about 0.10 to about 150 mg/day. In a particular embodiment, 4-(amino)-2-(2,6-dioxo(3-piperidyl))-isoindoline-1,3-dione (Actimid™) may be administered in an amount of from about 0.1 to about 1 mg per day, or alternatively from about 0.1 to about 5 mg every other day. In a preferred embodiment, 3-(4-amino-1-oxo-1,3-dihydro-isoindol-2-yl-piperidine-2,6-dione (Revimid™) may be administered in an amount of from about 5 to 25 mg per day, or alternatively from about 10 to about 50 mg every other day.

In a specific embodiment, 4-(amino)-2-(2,6-dioxo(3-piperidyl))-isoindoline-1,3-dione (Actimid™) may be administered in an amount of about 1, 2, or 5 mg per day to patients with relapsed multiple myeloma. In a particular embodiment, 3-(4-amino-1-oxo-1,3-dihydro-isoindol-2-yl)-piperidine-2,6-dione (Revimid™) may be administered initially in an amount of 5 mg/day and the dose can be escalated every week to 10, 20, 25, 30 and 50 mg/day. In a specific embodiment, Revimid™ can be administered in an amount of up to about 30 mg/day to patients with solid tumor. In a particular embodiment, Revimid™ can be administered in an amount of up to about 40 mg/day to patients with glioma.

5.3.1 Combination Therapy with a Second Active Agent

Specific methods of the invention comprise administering an immunomodulatory compound of the invention, or a pharmaceutically acceptable salt, solvate, hydrate, stereoisomer, clathrate, or prodrug thereof, in combination with one or more second active agents, and/or in combination with radiation therapy, blood transfusions, or surgery. Examples of immunomodulatory compounds of the invention are disclosed herein (see, e.g., section 5.1). Examples of second active agents are also disclosed herein (see, e.g., section 5.2).

Administration of the immunomodulatory compounds and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for an immunomodulatory compound of the invention is orally. Preferred routes of administration for the second active agents or ingredients of the invention are known to those of ordinary skill in the art. See, e.g., *Physicians' Desk Reference,* 1755-1760 (56$^{th}$ ed., 2002).

In one embodiment of the invention, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of immunomodulatory compounds of the invention and any optional additional active agents concurrently administered to the patient. In a particular embodiment, the second active agent is oblimersen (Genasense®), GM-CSF, G-CSF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine, or a combination thereof.

In a particular embodiment, GM-CSF, G-CSF or EPO is administered subcutaneously during about five days in a four or six week cycle in an amount of from about 1 to about 750 mg/m$^2$/day, preferably in an amount of from about 25 to about 500 mg/m$^2$/day, more preferably in an amount of from about 50 to about 250 mg/m$^2$/day, and most preferably in an amount of from about 50 to about 200 mg/m$^2$/day. In a certain embodiment, GM-CSF may be administered in an amount of from about 60 to about 500 mcg/m$^2$ intravenously over 2 hours, or from about 5 to about 12 mcg/m2/day subcutaneously. In a specific embodiment, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In a certain embodiment, EPO may be administered subcutaneously in an amount of 10,000 Unit 3 times per week.

In another embodiment, Revimid™ in an amount of about 25 mg/d and dacarbazine in an amount of about from 200 to 1,000 mg/m$^2$/d are administered to patients with metastatic malignant melanoma. In a specific embodiment, Revimid™ is administered in an amount of from about 5 to about 25 mg/d to patients with metastatic malignant melanoma whose disease has progressed on treatment with dacarbazine, IL-2 or IFN. In a specific embodiment, Revimid™ is administered to patients with relapsed or refractory multiple myeloma in an amount of about 15 mg/d twice a day or about 30 mg/d four times a day in a combination with dexamethasone.

In another embodiment, an immunomodulatory compound is administered with melphalan and dexamethasone to patients with amyloidosis. In a specific embodiment, an immunomodulatory compound of the invention and steroids can be administered to patients with amyloidosis.

In another embodiment, an immunomodulatory compound is administered with gemcitabine and cisplatinum to patients with locally advanced or metastatic transitional cell bladder cancer.

In another embodiment, an immunomodulatory compound is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapased brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In another embodiment, an immunomodulatory compound is administered with methotrexate and cyclophosphamide to patients with metastatic breast cancer.

In another embodiment, an immunomodulatory compound is administered with temozolomide to patients with neuroendocrine tumors.

In another embodiment, an immunomodulatory compound is administered with gemcitabine to patients with recurrent or metastatic head or neck cancer. In another embodiment, an immunomodulatory compound is administered with gemcitabine to patients with pancreatic cancer.

In another embodiment, an immunomodulatory compound is administered to patients with colon cancer in combination with Arisa®, taxol and/or taxotere.

In another embodiment, an immunomodulatory compound is administered with capecitabine to patients with refractory colorectal cancer or patients who fail first line therapy or have poor performance in colon or rectal adenocarcinoma.

In another embodiment, an immunomodulatory compound is administered in combination with fluorouracil, leucovorin, and irinotecan to patients with Dukes C & D colorectal cancer or to patients who have been previously treated for metastatic colorectal cancer.

In another embodiment, an immunomodulatory compound is administered to patients with refractory colorectal cancer in combination with capecitabine, xeloda, and/or CPT-11.

In another embodiment, an immunomodulatory compound of the invention is administered with capecitabine and irinotecan to patients with refractory colorectal cancer or to patients with unresectable or metastatic colorectal carcinoma.

In another embodiment, an immunomodulatory compound is administered alone or in combination with interferon alpha or capecitabine to patients with unresectable or metastatic hepatocellular carcinoma; or with cisplatin and thiotepa to patients with primary or metastatic liver cancer.

In another embodiment, an immunomodulatory compound is administered in combination with pegylated interferon alpha to patients with Kaposi's sarcoma.

In another embodiment, an immunomodulatory compound is administered in combination with fludarabine, carboplatin, and/or topotecan to patients with refractory or relapsed or high-risk acuted myelogenous leukemia.

In another embodiment, an immunomodulatory compound is administered in combination with liposomal daunorubicin, topotecan and/or cytarabine to patients with unfavorable karotype acute mycloblastic leukemia.

In another embodiment, an immunomodulatory compound is administered in combination with gemcitabine and irinotecan to patients with non-small cell lung cancer. In one embodiment, an immunomodulatory compound is administered in combination with carboplatin and irinotecan to patients with non-small cell lung cancer. In one embodiment, an immunomodulatory compound is administered with doxetaxol to patients with non-small cell lung cancer who have been previously treated with carbo/VP 16 and radiotherapy.

In another embodiment, an immunomodulatory compound is administered in combination with carboplatin and/or taxotere, or in combination with carboplatin, paclitaxel and/or thoracic radiotherapy to patients with non-small cell lung cancer. In a specific embodiment, an immunomodulatory compound is administered in combination with taxotere to patients with stage IIIB or IV non-small cell lung cancer.

In another embodiment, an immunomodulatory compound of the invention is administered in combination with oblimersen (Genasense®) to patients with small cell lung cancer.

In another embodiment, an immunomodulatory compound is administered alone or in combination with a second active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In another embodiment, an immunomodulatory compound is administered in combination with taxotere, IL-2, IFN, GM-CSF, and/or dacarbazine to patients with various types or stages of melanoma.

In another embodiment, an immunomodulatory compound is administered alone or in combination with vinorelbine to patients with malignant mesothelioma, or stage IIIB non-small cell lung cancer with pleural implants or malignant pleural effusion mesothelioma syndrome.

In another embodiment, an immunomodulatory compound is administered to patients with various types or stages of multiple myeloma in combination with dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, or a combination thereof.

In another embodiment, an immunomodulatory compound is administered to patients with relapsed or refractory multiple myeloma in combination with doxorubicin (Doxil®), vincristine and/or dexamethasone (Decadron®).

In another embodiment, an immunomodulatory compound is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In another embodiment, an immunomodulatory compound is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, or a combination thereof.

In another embodiment, an immunomodulatory compound is administered to patients with various types or stages of renal cell cancer, in combination with capecitabine, IFN, tamoxifen, IL-2, GM-CSF, Celebrex®, or a combination thereof.

In another embodiment, an immunomodulatory compound is administered to patients with various types or stages of gynecologic, uterus or soft tissue sarcoma cancer in combination with IFN, a COX-2 inhibitor such as Celebrex®, and/or sulindac.

In another embodiment, an immunomodulatory compound is administered to patients with various types or stages of solid tumors in combination with celebrex, etoposide, cyclophosphamide, docetaxel, apecitabine, IFN, tamoxifen, IL-2, GM-CSF, or a combination thereof.

In another embodiment, an immunomodulatory compound is administered to patients with scelrodenna or cutaneous vasculitis in combination with celebrex, etoposide, cyclophosphamide, docetaxel, apecitabine, IFN, tamoxifen, IL-2, GM-CSF, or a combination thereof.

This invention also encompasses a method of increasing the dosage of an anti-cancer drug or agent that can be safely and effectively administered to a patient, which comprises administering to a patient (e.g., a human) an immunomodulatory compound of the invention, or a pharmaceutically acceptable derivative, salt, solvate, clathrate, hydrate, or prodrug thereof. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of an immunomodulatory compound of the invention alleviates or reduces adverse effects which are of such severity that it would otherwise limit the amount of anti-cancer drug.

In one embodiment, an immunomodulatory compound of the invention can be administered orally and daily in an amount of from about 0.1 to about 150 mg, and preferably from about 1 to about 50 mg, more preferably from about 2 to about 25 mg prior to, during, or after the occurrence of the adverse effect associated with the administration of an anti-cancer drug to a patient. In a particular embodiment, an immunomodulatory compound of the invention is administered in combination with specific agents such as heparin, aspirin, coumadin, or G-CSF to avoid adverse effects that are associated with anti-cancer drugs such as but not limited to neutropenia or thrombocytopenia.

In one embodiment, an immunomodulatory compound of the invention can be administered to patients with diseases and disorders associated with, or characterized by, undesired angiogenesis in combination with additional active ingredients including but not limited to anti-cancer drugs, anti-inflammatories, antihistamines, antibiotics, and steroids.

In another embodiment, this invention encompasses a method of treating, preventing and/or managing cancer, which comprises administering an immunomodulatory compound of the invention, or a pharmaceutically acceptable salt, solvate, hydrate, stereoisomer, clathrate, or prodrug thereof, in conjunction with (e.g. before, during, or after) conventional therapy including, but not limited to, surgery, immunotherapy, biological therapy, radiation therapy, or other non-drug based therapy presently used to treat, prevent or manage cancer. The combined use of the immunomodulatory compounds of the invention and conventional therapy may provide a unique treatment regimen that is unexpectedly effective in certain patients. Without being limited by theory, it is believed that immunomodulatory compounds of the invention may provide additive or synergistic effects when given concurrently with conventional therapy.

As discussed elsewhere herein, the invention encompasses a method of reducing, treating and/or preventing adverse or undesired effects associated with conventional therapy including, but not limited to, surgery, chemotherapy, radiation therapy, hormonal therapy, biological therapy and immunotherapy. One or more immunomodulatory compounds of the invention and other active ingredient can be administered to a patient prior to, during, or after the occurrence of the adverse effect associated with conventional therapy.

In one embodiment, an immunomodulatory compound of the invention can be administered in an amount of from about 0.1 to about 150 mg, and preferably from about 1 to about 25 mg, more preferably from about 2 to about 10 mg orally and daily alone, or in combination with a second active agent disclosed herein (see, e.g., section 5.2), prior to, during, or after the use of conventional therapy.

In a specific embodiment of this method, an immunomodulatory compound of the invention and doxetaxol are administered to patients with non-small cell lung cancer who were previously treated with carbo/VP 16 and radiotherapy.

5.3.2 Use with Transplantation Therapy

Compounds of the invention can be used to reduce the risk of Graft Versus Host Disease (GVHD). Therefore, the invention encompasses a method of treating, preventing and/or managing cancer, which comprises administering the immunomodulatory compound of the invention, or a pharmaceutically acceptable salt, solvate, hydrate, stereoisomer, clathrate, or prodrug thereof, in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of the immunomodulatory compound of the invention and transplantation therapy provides a unique and unexpected synergism. In particular, an immunomodulatory compound of the invention exhibits immunomodulatory activity that may provide additive or synergistic effects when given concurrently with transplantation therapy in patients with cancer.

An immunomodulatory compound of the invention can work in combination with transplantation therapy reducing complications associated with the invasive procedure of transplantation and risk of GVHD. This invention encompasses a method of treating, preventing and/or managing cancer which comprises administering to a patient (e.g., a human) an immunomodulatory compound of the invention, or a pharmaceutically acceptable salt, solvate, hydrate, stereoisomer, clathrate, or prodrug thereof, before, during, or after the transplantation of umbilical cord blood, placental blood, peripheral blood stem cell, hematopoietic stem cell preparation or bone marrow. Examples of stem cells suitable for use in the methods of the invention are disclosed in U.S. provisional patent application No. 60/372,348, filed Apr. 12, 2002 by R. Hariri et al., the entirety of which is incorporated herein by reference.

In one embodiment of this method, an immunomodulatory compound of the invention is administered to patients with multiple myeloma before, during, or after the transplantation of autologous peripheral blood progenitor cell.

In another embodiment, an immunomodulatory compound is administered to patients with relapsing multiple myeloma after the stem cell transplantation.

In another embodiment, an immunomodulatory compound and prednisone are administered as maintenance therapy to patients with multiple myeloma following the transplantation of autologous stem cell.

In another embodiment, an immunomodulatory compound and dexamethasone are administered as salvage therapy for low risk post transplantation to patients with multiple myeloma.

In another embodiment, an immunomodulatory compound and dexamethasone are administered as maintenance therapy to patients with multiple myeloma following the transplantation of autologous bone marrow.

In another embodiment, an immunomodulatory compound is administered following the administration of high dose of melphalan and the transplantation of autologous stem cell to patients with chemotherapy responsive multiple myeloma.

In another embodiment, an immunomodulatory compound and PEG INTRO-A are administered as maintenance therapy to patients with multiple myeloma following the transplantation of autologous CD34-selected peripheral stem cell.

In another embodiment, an immunomodulatory compound is administered with post transplant consolidation chemotherapy to patients with newly diagnosed multiple myeloma to evaluate anti-angiogenesis.

In another embodiment, an immunomodulatory compound and dexamethasone are administered as maintenance therapy after DCEP consolidation, following the treatment with high dose of melphalan and the transplantation of peripheral blood stem cell to 65 years of age or older patients with multiple myeloma.

5.3.3 Cycling Therapy

In certain embodiments, the prophylactic or therapeutic agents of the invention are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one specific embodiment of the invention, an immunomodulatory compound of the invention is administered daily in a single or divided doses in a four to six week cycle with a rest period of about a week or two weeks. The invention further allows the frequency, number, and length of dosing cycles to be increased. Thus, another specific embodiment of the invention encompasses the administration of an immunomodulatory compound of the invention for more cycles than are typical when it is administered alone. In yet another specific embodiment of the invention, an immunomodulatory compound of the invention is administered for a greater number of cycles that would typically cause dose-limiting toxicity in a patient to whom a second active ingredient is not also being administered.

In one embodiment, an immunomodulatory compound of the invention is administered daily and continuously for three or four weeks at a dose of from about 0.1 to about 150 mg/d followed by a break of one or two weeks. Actimid™ is preferably administered daily and continuously at an initial dose of 0.1 to 5 mg/d with dose escalation (every week) by 1 to 10 mg/d to a maximum dose of 50 mg/d for as long as therapy is tolerated. In a particular embodiment, Revimid™ is administered in an amount of about 5, 10, or 25 mg/day, preferably in an amount of about 10 mg/day for three to four weeks, followed by one week or two weeks of rest in a four or six week cycle.

In one embodiment of the invention, an immunomodulatory compound of the invention and a second active ingredient are administered orally, with administration of an immunomodulatory compound of the invention occurring 30 to 60 minutes prior to a second active ingredient, during a cycle of four to six weeks. In another embodiment of the invention, the combination of an immunomodulatory compound of the invention and a second active ingredient is administered by intravenous infusion over about 90 minutes every cycle. In a specific embodiment, one cycle comprises the administration of from about 10 to about 25 mg/day of Revimid™ and from about 50 to about 200 mg/m$^2$/day of a second active ingredient daily for three to four weeks and then one or two weeks of rest. In another specific embodiment, each cycle comprises the administration of from about 5 to about 10 mg/day of Actimid™ and from about 50 to about 200 mg/m²/day of a second active ingredient for 3 to 4 weeks followed by one or two weeks of rest. Typically, the number of cycles during which the combinatorial treatment is administered to a patient will be from about one to about 24 cycles, more typically from about two to about 16 cycles, and even more typically from about four to about three cycles.

5.4 Pharmaceutical Compositions and Dosage Forms

Pharmaceutical compositions can be used in the preparation of individual, single unit dosage forms. Pharmaceutical compositions and dosage forms of the invention comprise an immunomodulatory compound of the invention, or a pharmaceutically acceptable salt, solvate, hydrate, stereoisomer, clathrate, or prodrug thereof. Pharmaceutical compositions and dosage forms of the invention can further comprise one or more excipients.

Pharmaceutical compositions and dosage forms of the invention can also comprise one or more additional active ingredients. Consequently, pharmaceutical compositions and dosage forms of the invention comprise the active ingredients disclosed herein (e.g., an immunomodulatory compound and a second active agent). Examples of optional second, or additional, active ingredients are disclosed herein (see, e.g., section 5.2).

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise an immunomodulatory compound of the invention or a pharmaceutically acceptable salt, solvate, hydrate, stereoisomer, clathrate, or prodrug thereof in an amount of from about 0.10 to about 150 mg. Typical dosage forms comprise an immunomodulatory compound of the invention or a pharmaceutically acceptable salt, solvate, hydrate, stereoisomer, clathrate, or prodrug thereof in an amount of about 0.1, 1, 2, 5, 7.5, 10, 12.5, 15, 17.5, 20, 25, 50, 100, 150 or 200 mg. In a particular embodiment, a preferred dosage form comprises 4-(amino)-2-(2,6-dioxo(3-piperidyl))-isoindoline-1,3-dione (Actimid™) in an amount of about 1, 2, 5, 10, 25 or 50 mg. In a specific embodiment, a preferred dosage form comprises 3-(4-amino-1-oxo-1,3-dihydro-isoindol-2-yl)-piperidine-2,6-dione (Revimid™) in an amount of about 5, 10, 25 or 50 mg. Typical dosage forms comprise the second active ingredient in an amount of 1 to about 1000 mg, from about 5 to about 500 mg, from about 10 to about 350 mg, or from about 50 to about 200 mg. Of course, the specific amount of the anti-cancer drug will depend on the specific agent used, the type of cancer being treated or managed, and the amount(s) of an immunomodulatory compound of the invention and any optional additional active agents concurrently administered to the patient.

5.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, PA), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an immunomodulatory compound of the invention, anhydrous lactose, microcrystalline cellulose, polyvinylpyrrolidone, stearic acid, colloidal anhydrous silica, and gelatin.

5.4.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.4.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. For example, cyclodextrin and its derivatives can be used to increase the solubility of an immunomodulatory compound of the invention and its derivatives. See, e.g., U.S. Pat. No. 5,134,127, which is incorporated herein by reference.

5.4.4 Topical and Mucosal Dosage Forms

Topical and mucosal dosage forms of the invention include, but are not limited to, sprays, aerosols, solutions, emulsions, suspensions, eye drops or other ophthalmic preparations, or other forms known to one of skill in the art. See, e.g., *Remington's Pharmaceutical Sciences,* $16^{th}$ and $18^{th}$ eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences,* $16^{th}$ and $18^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5.4.5 Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a dosage form of an immunomodulatory compound of the invention, or a pharmaceutically acceptable salt salt, solvate, hydrate, stereoisomer, prodrug, or clathrate thereof. Kits encompassed by this invention can further comprise additional active ingredients such as oblimersen (Genasense®), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein (see, e.g., section 5.2).

Kits of the invention can further comprise devices that are used to administer the active ingredients. Examples of such devices include, but are not limited to, syringes, drip bags, patches, and inhalers.

Kits of the invention can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

6. EXAMPLES

Certain embodiments of the invention are illustrated by the following non-limiting examples.

6.1 Modulation of Cytokine Production

A series of non-clinical pharmacology and toxicology studies have been performed to support the clinical evaluation of an immunomodulatory compound of the invention in human subjects. These studies were performed in accordance with internationally recognized guidelines for study design and in compliance with the requirements of Good Laboratory Practice (GLP), unless otherwise noted.

Inhibition of TNF-α production following LPS-stimulation of human PBMC and human whole blood by 4-(amino)-2-(2,6-dioxo(3-piperidyl))-isoindoline-1,3-dione (Actimid™), 3-(4-amino-1-oxo-1,3-dihydro-isoindol-2-yl)-piperidine-2,6-dione and thalidomide (Revimid™) was investigated in vitro (Muller et al., Bioorg. Med. Chem. Lett. 9:1625-1630, 1999). The $IC_{50}$'s of 4-(amino)-2-(2,6-dioxo(3-piperidyl))-isoindoline-1,3-dione for inhibiting production of TNF-α following LPS-stimulation of PBMC and human whole blood were ~24 nM (6.55 ng/mL) and ~25 nM (6.83 ng/mL), respectively. In vitro studies suggest a pharmacological activity profile for 3-(4-amino-1-oxo-1,3-dihydro-isoindol-2-yl)-piperidine-2,6-dione that is similar to, but at least 200 times more potent than, thalidomide. In vitro studies have also demonstrated that concentrations of 4-(amino)-2-(2,6-dioxo(3-piperidyl))-isoindoline-1,3-dione of 2.73 to 27.3 ng/mL (0.01 to 0.1 µM) achieved 50% inhibition of the proliferation of MM.IS and Hs Sultan cells.

The $IC_{50}$'s of 3-(4-amino-1-oxo-1,3-dihydro-isoindol-2-yl)-piperidine-2,6-dione for inhibiting production of TNF-α following LPS-stimulation of PBMC and human whole blood were ~100 nM (25.9 ng/mL) and ~480 nM (103.6 ng/mL), respectively. Thalidomide, in contrast, had an $IC_{50}$ of ~194 µM (50.2 µg/mL) for inhibiting production of TNF-α following LPS-stimulation of PBMC. In vitro studies suggest a pharmacological activity profile for 3-(4-amino-1-oxo-1,3-dihydro-isoindol-2-yl)-piperidine-2,6-dione that is similar to, but 50 to 2000 times more potent than, thalidomide. It has been shown that the compound is approximately 50-100 times more potent than thalidomide in stimulating the proliferation of T-cells following primary induction by T-cell receptor (TCR) activation. 3-(4-amino-1-oxo-1,3-dihydro-isoindol-2-yl)-piperidine-2,6-dione is also approximately 50 to 100 times more potent than thalidomide in augmenting the production of IL-2 and IFN-γ following TCR activation of PBMC (IL-2) or T-cells (IFN-γ). In addition, 3-(4-amino-1-oxo-1,3-dihydro-isoindol-2-yl)-piperidine-2,6-dione exhibited dose-dependent inhibition of LPS-stimulated production of the pro-inflammatory cytokines TNF-α, IL-1β, and IL-6 by PBMC while it increased production of the anti-inflammatory cytokine IL-10.

6.2 Inhibition of MM Cell Proliferation

The ability of 3-(4-amino-1-oxo-1,3-dihydro-isoindol-2-yl)-piperidine-2,6-dione (Revimid™) and thalidomide for comparison to effect the proliferation of MM cell lines has been investigated in an in vitro study. Uptake [$^3$H]-thymidine by different MM cell lines (MM.1S, Hs Sultan, U266 and RPMI-8226) was measured as an indicator of cell proliferation. Cells were incubated in the presence of compounds for 48 hours; [$^3$H]-thymidine was included for the last 8 hours of the incubation period. Addition of 3-(4-amino-1-oxo-1,3-dihydro-isoindol-2-yl)-piperidine-2,6-dione to MM. 1S and Hs Sultan cells resulted in 50% inhibition of cell proliferation at concentrations of 0.4 µm and 1 µm, respectively. In contrast, addition of thalidomide at concentrations up to 100 µm resulted in only 15% and 20% inhibition of cell proliferation in MM.1S and Hs Sultan cells, respectively. These data are summarized in FIG. 1.

6.3 Toxicology Studies

The effects of 3-(4-amino-1-oxo-1,3-dihydro-isoindol-2-yl)-piperidine-2,6-dione (Revimid™) on cardiovascular and respiratory function are investigated in anesthetized dogs. Two groups of Beagle dogs (2/sex/group) are used. One group receives three doses of vehicle only and the other receives three ascending doses of 3-(4-amino-1-oxo-1,3-dihydro-isoindol-2-yl)-piperidine-2,6-dione (2, 10, and 20 mg/kg). In all cases, doses of 3-(4-amino-1-oxo-1,3-dihydro-isoindol-2-yl)-piperidine-2,6-dione or vehicle are successively administered via infusion through the jugular vein separated by intervals of at least 30 minutes.

The cardiovascular and respiratory changes induced by 3-(4-amino-1-oxo-1,3-dihydro-isoindol-2-yl)-piperidine-2,6-dione are minimal at all doses when compared to the vehicle control group. The only statistically significant difference between the vehicle and treatment groups is a small increase in arterial blood pressure (from 94 mmHg to 101 mmHg) following administration of the low dose of 3-(4-amino-1-oxo-1,3-dihydro-isoindol-2-yl)-piperidine-2,6-dione. This effect lasts approximately 15 minutes and is not seen at higher doses. Deviations in femoral blood flow, respiratory parameters, and Qtc interval are common to both the control and treated groups and are not considered treatment-related.

6.4 Cycling Therapy in Patients

In a specific embodiment, an immunomodulatory compound of the invention are cyclically administered to patients with cancer. Cycling therapy involves the administration of a first agent for a period of time, followed by a rest for a period of time and repeating this sequential administration. Cycling therapy can reduce the development of resistance to one or more of the therapies, avoid or reduce the side effects of one of the therapies, and/or improves the efficacy of the treatment.

In a specific embodiment, prophylactic or therapeutic agents are administered in a cycle of about 4 to 6 weeks, about once or twice every day. One cycle can comprise the administration of a therapeutic on prophylactic agent for three to four weeks and at least a week or two weeks of rest. The number of cycles administered is from about one to about 24 cycles, more typically from about two to about 16 cycles, and more typically from about four to about eight cycles.

For example, in a cycle of four weeks, on day 1, the administration of 25 mg/d of 3-(4-amino-1-oxo-1,3-dihydro-isoindol-2-yl)-piperidine-2,6-dione is started. On day 22, the administration of the compound is stopped for a week of rest. On day 29, the administration of 25 mg/d 3-(4-amino-1-oxo-1,3-dihydro-isoindol-2-yl)-piperidin-2,6-dione is begun.

6.5 Clinical Studies in Patients 6.5.1 Treatment of Relapsed Multiple Myeloma 4-(amino)-2-(2,6-dioxo(3-piperidyl))-isoindoline-1,3-dione (Actimid™) was administered to patients with relapsed/refractory multiple myeloma. The study was conducted in compliance with Good Clinical Practices. Patients were at least 18 years old, had been diagnosed with multiple myeloma (with paraprotein in serum and/or urine), and were considered refractory to treatment after at least two cycles of treatment, or have relapsed after two cycles of treatment.

Patients who have progressive disease, according to the Southwest Oncology Group (SWOG) criteria, on their prior regimen are considered treatment refractory. Relapse following remission is defined as >25% increase in M component from baseline levels; reappearance of the M paraprotein that had previously disappeared; or a definite increase in the size and number of lytic bone lesions recognized on radiographs. Patients may have had prior therapy with thalidomide, provided they were able to tolerate the treatment. A Zubrod performance status of 0 to 2 is required for all patients.

4-(amino)-2-(2,6-dioxo(3-piperidyl))-isoindoline-1,3-dione is administered to patients at doses of 1, 2, 5, or 10 mg/day for up to four weeks; at each dose level, three patients are initially enrolled. Dosing occurs at approximately the same time each morning; all doses are administered in the fasted state (no eating for at least two hours prior to dosing and two hours after dosing). 4-(amino)-2-(2,6-dioxo(3-piperidyl))-isoindoline-1,3-dione doses are administered in an ascending fashion such that patients in the first cohort receive the lowest dose of 4-(amino)-2-(2,6-dioxo(3-piperidyl))-isoindoline-1,3-dione (1 mg/day) and escalation to the next higher dose level occurs only following the establishment of safety and tolerability at the current dose. If one out of three patients at any dose level experience dose limiting toxicity (DLT), three additional patients are enrolled at that dose. If none of the three additional patients experience DLT, escalation to the next dose level occurs; dose escalations continue in a similar fashion until the MTD is established or the maximum daily dose (10 mg/day) is attained. However, if one of the three additional patients enrolled experiences DLT, the MTD has been reached. If two or more of the three additional patients enrolled experience DLT, the MTD is judged to have been exceeded and three additional patients are enrolled at the preceding dose level to confirm the MTD. Once the MTD has been identified, four additional patients are enrolled at that dose level so that a total of 10 patients is treated at the MTD.

Blood sampling for analysis of pharmacokinetic parameters is performed on Days 1 and 28 according to the following sampling schedule: pre-dose, 0.25, 0.5, 0.75, 1, 1.5, 2, 2.5, 3, 4, 6, 8, 10, 12, 18, and 24 hours post-dose. An additional blood sample is collected at each weekly visit for the determination of 4-(amino)-2-(2,6-dioxo(3-piperidyl))-isoindoline-1,3-dione levels. Total urine collections are also made with urine pooled according to the following time intervals post-dose: 0 to 4, 4 to 8, 8 to 12, and 12 to 24 hours. Safety assessments are made by monitoring adverse events, vital signs, ECGs, clinical laboratory evaluations (blood chemistry, hematology, lymphocyte phenotyping, and urinalysis), and physical examination at specific times during the study.

Results of interim pharmacokinetic analyses obtained following single- and multiple-dose administration of 4-(amino)-2-(2,6-dioxo(3-piperidyl))-isoindoline-1,3-dione to multiple myeloma patients are presented below in Tables 1 and 2. These data show that 4-(amino)-2-(2,6-dioxo(3-piperidyl))-isoindoline-1,3-dione was steadily absorbed at all dose levels in relapsed multiple myeloma patients. Maximum plasma concentrations occurred at a median $T_{max}$ of between 2.5 and 2.8 hours post-dose at Day 1 and between 3 and 4 hours post-dose at Week 4. At all doses, plasma concentrations declined in a monophasic manner after reaching $C_{max}$. The start of the elimination phase occurred between 3 and 10 hours post-dose at Day 1 and Week 4, respectively.

These data also showed that after 4 weeks of dosing, 4-(amino)-2-(2,6-dioxo(3-piperidyl))-isoindoline-1,3-dione accumulated to a small extent (mean accumulation ratios ~1.02 to 1.52 and ~0.94 to 1.62 for $C_{max}$ and $AUC_{(0-\tau)}$, respectively). There was almost a dose proportional increase in $AUC_{(0-\tau)}$ and $C_{max}$ values with increasing dose. A five-fold higher dose of 4-(amino)-2-(2,6-dioxo(3-piperidyl))-isoindoline-1,3-dione produced a 3.2- and 2.2-fold increase in $C_{max}$ at Day 1 and Week 4, respectively. Similarly, a 5-fold increase in dose resulted in a 3.6- and 2.3-fold increase in $AUC_{(0-\tau)}$, at Day 1 and Week 4, respectively.

TABLE 1

Pharmacokinetic parameters of Actimid ™ in relapsed multiple myeloma patients

| Parameter | | 1 mg (N = 6) | 2 mg (N = 2) | 5 mg (N = 3) |
|---|---|---|---|---|
| | | Day 1 | | |
| $C_{max}$ | ng/mL | 15.03 (4.04) | 24.4* (12.1) | 48.56 (14.03) |
| $t_{max}$ | h | 3.3 (2.6) | 2.7* (0.3) | 2.3 (0.3) |
| $AUC_{(0-\infty)}$ | ng.h/mL | 152.90 (36.62) | 279.18 (51.10) | 593.10 (335.23) |
| $AUC_{(0-\tau)}$ | | 134.21 (27.14) | 249.57 (29.26) | 520.94 (267.32) |
| $t^{1/2}$ | h | 7.3 (3.4) | 6.3 (1.4) | 6.5 (2.2) |
| CL/F | mL/min | 114.75 (29.20) | 121.43 (22.22) | 182.31 (117.06) |
| Vz/f | L | 69.55 (44.97) | 65.31 (2.80) | 87.24 (22.61) | t = 24 hours

N/A = not available

TABLE 2

Pharmacokinetic parameters of Actimid ™ following multiple oral doses (1, 2, and 5 mg/day) in relapsed multiple myeloma patients

| Parameter | | 1 mg (N = 5) | 2 mg (N = 2) | 5 mg (N = 3) |
|---|---|---|---|---|
| | | Week 4 | | |
| $C_{max}$ | ng/mL | 23.20 (7.48) | 30.05* (15.64) | 58.07 (38.08) |
| $t_{max}$ | h | 3.6 (1.5) | 2.8* (0.3) | 5.0 (2.6) |
| $AUC_{(0-\infty)}$ | ng.h/mL | N/A | N/A | N/A |
| $AUC_{(0-\tau)}$ | | 239.31 (122.59) | 269.36 (186.34) | 597.24 (354.23) |
| $t^{1/2}$ | h | 6.2* (0.6) | 7.7 (2.8) | 7.8 (4.0) |
| CL/F | mL/min | 87.85 (48.48) | 162.68 (112.54) | 207.50 (175.41) |
| Vz/f | L | 41.35* (8.84) | 95.04 (35.39) | 103.95 (27.25) |

$\tau$ = 24 hours
N/A = not available
*N = 3 patients

6.5.2 Treatment of Relapsed Multiple Myeloma

Two Phase 1 clinical studies of 3-(4-amino-1-oxo-1,3-dihydro-isoindol-2-yl)-piperidine-2,6-dione (Revimid™) have been conducted to identify the maximum tolerated dose (MTD) in patients with refractory or relapsed multiple myeloma. These studies have also characterized the safety profile of 3-(4-amino-1-oxo-1,3-dihydro-isoindol-2-yl)-piperidine-2,6-dione when ascending doses of 3-(4-amino-1-oxo-1,3-dihydro-isoindol-2-yl)-piperidine-2,6-dione were given orally for up to 4 weeks. Patients started 3-(4-amino-1-oxo-1,3-dihydro-isoindol-2-yl)-piperidine-2,6-dione treatment at 5 mg/day with subsequent escalation to 10, 25, and 50 mg/day. Patients were enrolled for 28 days at their assigned dose, with the option of extended treatment for those who did not exhibit disease progression or experience dose limiting toxicity (DLT). Patients were evaluated for adverse events at each visit and the severity of these events was graded according to the National Cancer Institute (NCI) Common Toxicity Criteria. Patients were discontinued if they experienced DLT (Grade 3 or greater non-hematological, or Grade 4 hematological toxicity).

In this study, 27 patients were enrolled. All patients had relapsed multiple mycloma and 18 (72%) were refractory to salvage therapy. Among these patients, 15 had undergone prior autologous stem cell transplantation and 16 patients had received prior thalidomide treatment. The median number of prior regimens was 3 (range 2 to 6).

Blood and urine samples were collected for analysis of pharmacokinetic parameters on Days 1 and 28. Blood samples were collected according to the following sampling schedule: pre-dose, 0.25, 0.5, 0.75, 1, 1.5, 2, 2.5, 3, 4, 6, 8, 10, 12, 18, and 24 hours post-dose. In addition, a blood sample was collected at each weekly clinic visit for 3-(4-amino-1-oxo-1,3-dihydro-isoindol-2-yl)-piperidine-2,6-dione determination. Total urine was collected and pooled according to the following time intervals post-dose: 0 to 4, 4 to 8, 8 to 12, and 12 to 24 hours. Response to treatment was assessed by M-protein quantification (by immunoelectrophoresis) from serum and a 24-hour urine collection, with creatinine clearance and 24-hour protein calculations undertaken at screening, baseline, Weeks 2 and 4, and monthly thereafter (or upon early termination). Bone marrow aspirations and/or tissue biopsy are also performed at Months 3, 6 and 12 if a patient's paraprotein serum concentration or 24-hour urine protein excretion declined to the next lower level, based on best response criteria. Preliminary results for the 28-day treatment period are summarized below.

Preliminary pharmacokinetic analyses based on these two studies indicated that AUC and $C_{max}$ values increase proportionally with dose following single and multiple doses in multiple myeloma patients (as was seen in healthy volunteers). Further, there was no evidence of accumulation with multiple dosing as single dose $AUC_{(0-\infty)}$ was comparable to multiple dose $AUC_{0-\tau}$ following the same dose of 3-(4-amino-1-oxo-1,3-dihydro-isoindol-2-yl)-piperidine-2,6-dione. Similar to healthy volunteer studies, double peaks were observed. Exposure in multiple myeloma patients appeared to be slightly higher based on $C_{max}$ and AUC values as compared to healthy male volunteers while clearance in multiple myeloma patients was lower than it was in healthy volunteers, consistent with their poorer renal function (both as a consequence of their age and their disease). Finally, 3-(4-amino-1-oxo-1,3-dihydro-isoindol-2-yl)-piperidine-2,6-dione half-live in patients was shorter than in healthy volunteers (mean 8 hours, ranging up to 17 hours).

In this study, the first cohort of 3 patients was treated for 28 days at 5 mg/day without any dose limiting toxicity (DLT). The second cohort of 3 patients subsequently commenced therapy at 10 mg/day. Patients in the second 10 mg/day of 3-(4-amino-1-oxo-1,3-dihydro-isoindol-2-yl)-piperidine-2,6-dione cohort tolerated treatment well.

6.5.3 Treatment of Solid Tumors

Study with 3-(4-amino-1-oxo-1,3-dihydro-isoindol-2-yl)-piperidine-2,6-dione (Revimid™) was conducted in patients with varying types of solid tumors, including malignant melanoma (13), carcinoma of the pancreas (2), carcinoid-unknown primary (1), renal carcinoma (1), breast carcinoma (1) and NSCLC (2). Patients received 5 mg/day 3-(4-amino-1-oxo-1,3-dihydro-isoindol-2-yl)-piperidine-2,6-dione for seven days and are subsequently escalated every seven days to 10 mg/day, 25 mg/day, and 50 mg/day for a total of 4 weeks of treatment. Patients who, experienced clinical benefit were permitted to continue on treatment as Named Patients.

The study initially enrolled 20 patients and was subsequently amended to enroll 16 additional patients (adrenal carcinoma, NSCLC, malignant mesothelioma, breast cancer, malignant melanoma (8), renal cell cancer (4)) at a higher dose. The 16 additional patients were given weekly escalating doses of 25 mg/day, 50 mg/day, 75 mg/day, 100 mg/day, 125 mg/day, and 150 mg/day over a 6-week period with continuing treatment for an additional six weeks.

The study of Phase 1 study was designed to determine a maximum tolerated dose (MTD) of 3-(4-amino-1-oxo-1,3-dihydro-isoindol-2-yl)-piperidine-2,6-dione in patients with refractory solid tumors and/or lymphoma, as well as to characterize the pharmacokinetic and side effect profiles of 3-(4-amino-1-oxo-1,3-dihydro-isoindol-2-yl)-piperidine-2,6-dione in this patient population. The study design dictates that at least 3 patients must be enrolled at a dose level and have completed 28 days of treatment prior to enrollment of patients at the next higher dose level. Patients in the first cohort began dosing at 5 mg/day of 3-(4-amino-1-oxo-1,3-dihydro-isoindol-2-yl)-piperidine-2,6-dione. Patients will be escalated to 10, 20, 25, and 30 mg/day provided there is no toxicity.

In this study, the MTD is defined as the highest dose level in which fewer than two of six patients treated did not experience Grade 3 or greater non-hematological toxicity or Grade 4 or greater hematological toxicity. If, at any given dose level in either study, one out of three patients experiences toxicity, three additional patients must be treated at that particular dose. If, however, two out of six patients experience DLT, the MTD is judged to have been exceeded. No further dose escalations are to occur and additional patients are to be enrolled at the previous dose level. The dose of 3-(4-amino-1-oxo-1,3-dihydro-isoindol-2-yl)-piperidine-2,6-dione administered is escalated until the MTD is achieved or the maximum daily dose of is reached.

No DLTs were reported in the initial group of 20 patients enrolled in the study. Thirteen of the original 20 trial patients, along with 2 non-trial patients, continued on treatment as named patients at doses up to 150 mg/day.

6.5.4 Treatment of Gliomas

This study was performed to find toxicity in patients with recurrent, high-grade gliomas. The study is designed such that patients are given increasingly higher doses of 3-(4-amino-1-oxo-1,3-dihydro-isoindol-2-yl)-piperidine-2,6-dione until a maximum tolerated dose (MTD) is established. The study also seeks to obtain preliminary toxicity information and pharmacokinetic data on 3-(4-amino-1-oxo-1,3-dihydro-isoindol-2-yl)-piperidine-2,6-dione, as well as to develop exploratory data concerning surrogate end points of angiogenic activity in vivo using functional neuro-imaging studies, and in vitro assays of serum angiogenic peptides.

Patients enrolled in the first cohort receive 2.5 mg/m$^2$/day for a 4-week cycle. During each 4-week cycle of therapy, 3-(4-amino-1-oxo-1,3-dihydro-isoindol-2-yl)-piperidine-2,6-dione administered once daily for 3 weeks followed by a week of rest. Patients who complete a treatment cycle may receive another cycle of 3-(4-amino-1-oxo-1,3-dihydro-isoindol-2-yl)-piperidine-2,6-dione treatment if two criteria are met. First, the patient must have stable disease or have experienced a partial response or complete response, or the patient is benefiting from the therapy with 3-(4-amino-1-oxo-1,3-dihydro-isoindol-2-yl)-piperidine-2,6-dione as evidenced by a decrease in tumor-related symptoms such as neurological deficits. Second, the patient must have recovered from toxicity related to 3-(4-amino-1-oxo-1,3-dihydro-isoindol-2-yl)-piperidine-2,6-dione which occurred in the prior cycle by Day 42 or sooner (28-day cycle plus limit of 2 weeks to recover) as evidenced by a return to Grade $\leq 1$ toxicity level. Patients who experience DLT in the previous cycle should have their dose modified. DLT is defined as an non-hematological event Grade $\geq 3$ toxicity or hematological event of Grade 4 toxicity thought to be related to the study medication. Patients who experience DLT in the first cycle and have no response to therapy are removed from the study.

3-(4-amino-1-oxo-1,3-dihydro-isoindol-2-yl)-piperidine-2,6-dione doses are subsequently escalated to 5, 8, 11, 15, and 20 mg/m$^2$/day to a maximum total daily dose of 40 mg. Patients continue to receive 3-(4-amino-1-oxo-1,3-dihydro-isoindol-2-yl)-piperidine-2,6-dione on a 4-week cycle per dose level until one of the off-study criteria are met.

Three patients are enrolled in each cohort. If at least one DLT occurs, three additional patients are added to the cohort at that particular dose level. If two DLTs occur, the MTD, defined as the dose at which fewer than one-third of patients at each dose level experiences DLT has been exceeded and four more patients are treated at the previous dose.

Patients who experience DLT during the first 4-week cycle are removed from the study, except if they have a response to therapy. For patients who have completed their first 4-week cycle of without DLT, but who subsequently experience Grade 3 or 4 hematological and/or nonhematological toxicity, treatment is suspended for a minimum of a week. If the toxicity resolves to <Grade 2 within three weeks, the patient is treated at two dose levels lower than the dose that caused the toxicity (or a 50% reduction if the patient was treated at the first or second dose level). Patients in whom Grade 3 or 4 toxicity does not resolve to <Grade 1 within three weeks, or those who have another Grade 3 toxicity at the reduced dose are removed from the study.

Pharmacokinetic sampling is performed prior the first dose of 3-(4-amino-1-oxo-1,3-dihydro-isoindol-2-yl)-piperidine-2,6-dione (Day 1) and 0.5, 1, 2, 4, 6, 8, 24, and 48 hours thereafter. Sampling is also conducted pre-dose on Days 7 and 21 and 0.5, 1, 2, 4, 6, 8, and 24 post-dose on Day 21 to evaluate steady-state 3-(4-amino-1-oxo-1,3-dihydro-isoindol-2-yl)-piperidine-2,6-dione levels.

6.5.5 Treatment of Metastatic Melanoma

Patients with metastatic melanoma were started on 3-(4-amino-1-oxo-1,3-dihydro-isoindol-2-yl)-piperidine-2,6-dione (Revmid™) at 5 mg/day for seven days. The dose was then increased every seven days to 10 mg/day, 25 mg/day, and 50 mg/day, respectively, for a total of four weeks on therapy. Five of the 13 melanoma patients who were treated under this regimen either showed disease stabilization or a partial response in the first four weeks of treatment. Tumor response was seen in cutaneous and subcutaneous lesions (five patients), lymph nodes (two patients), and liver (one patient). The duration of response was approximately six months. The result suggests that the compound appears is a promising new anti-cancer agent and has both antiangiogenic and immunomodulatory properties.

6.5.6 Treatment of Relapsed or Refractory Multiple Myeloma

Patients with relapsed and refractory Dune-Salmon stage III multiple myeloma, who have either failed at least three previous regimens or presented with poor performance status, neutropenia or thrombocytopenia, are treated with up to four cycles of combination of melphalan (50 mg intravenously), an immunomodulatory compound of the invention (about 1 to 150 mg orally daily), and dexamethasone (40 mg/day orally on days 1 to 4) every four to six weeks. Maintenance treatment consisting of daily an immunomodulatory compound of the invention and monthly dexamethasone are continued until the disease progression. The therapy using an immunomodulatory compound of the invention in combination with melphalan and dexamethasone is highly active and generally tolerated in heavily pretreated multiple myeloma patients whose prognosis is otherwise poor.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating multiple myeloma, which comprises cyclically administering to a patient having multiple myeloma about 5 to about 25 mg per day of a compound of the formula:

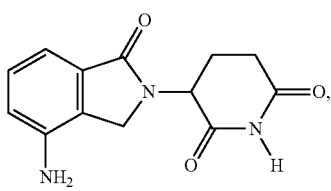

or a pharmaceutically acceptable salt thereof, for 21 consecutive days followed by seven in combination with 40 mg per day dexamethasone.

2. The method of claim 1, wherein the multiple myeloma is smoldering myeloma, indolent myeloma, chemotherapy responsive multiple myeloma, refractory myeloma, relapsed myeloma, or relapsed and refractory Dune-Salmon stage III multiple myeloma.

3. The method of claim 1, wherein the compound is a pharmaceutically acceptable salt.

4. The method of claim 1, wherein the multiple myeloma is relapsed, refractory or resistant to previous therapy.

5. The method of claim 1, wherein the compound and dexamethasone are administered orally.

6. The method of claim 5, wherein the compound is administered in the form of a capsule or tablet.

7. The method of claim 1, wherein the compound is administered in an amount of from about 10 to about 25 mg per day.

8. The method of claim 1, wherein the compound is administered in an amount of about 5, 10, 20, or 25 mg per day.

9. The method of claim 7, wherein the compound is administered in an amount of about 25 mg per day.

10. The method of claim 1, wherein the compound is administered in an amount of 5 mg per day.

11. The method of claim 7, wherein the compound is administered in an amount of 10 mg per day.

12. The method of claim 1, wherein the compound is administered in a capsule of 5 mg, 10 mg, 15 mg or 25 mg.

13. A method of treating multiple myeloma, which comprises administering, on a 28 day cycle, to a patient having multiple myeloma:

(a) about 25 mg per day of a compound of the formula:

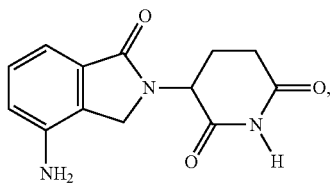

or a pharmaceutically acceptable salt thereof, for 21 consecutive days followed by seven consecutive days of rest from administration of said compound, and; (b) 40 mg per day of dexamethasone on days 1-4 every 28 days.

14. The method of claim 12, wherein the capsule comprises the compound, lactose anhydrous, microcrystalline cellulose, croscarmellose sodium and magnesium stearate.

15. The method of claim 1, wherein said dexamethasone is administered.

* * * * *

UNITED STATES PATENT AND TRADEMARK OFFICE
CERTIFICATE OF CORRECTION

| | | |
|---|---|---|
| PATENT NO. | : 7,968,569 B2 | Page 1 of 1 |
| APPLICATION NO. | : 10/438213 | |
| DATED | : June 28, 2011 | |
| INVENTOR(S) | : Jerome B. Zeldis | |

It is certified that error appears in the above-identified patent and that said Letters Patent is hereby corrected as shown below:

In claim 1, at column 39, line 11, after "followed by seven", insert -- consecutive days of rest from administration of said compound during a 28 day cycle, --

In claim 1, at column 39, line 12, between "day" and "dexamethasone", insert -- of --

In claim 15, at column 40, line 30, after "administered", insert -- orally --

Signed and Sealed this
Ninth Day of August, 2011

David J. Kappos
*Director of the United States Patent and Trademark Office*